United States Patent
Bestor et al.

(10) Patent No.: US 9,738,922 B2
(45) Date of Patent: Aug. 22, 2017

(54) UNIVERSAL METHYLATION PROFILING METHODS

(71) Applicants: Timothy H. Bestor, New York, NY (US); John R. Edwards, St. Louis, MO (US); Jingyue Ju, Englewood Cliffs, NJ (US); Xiaoxu Li, New York, NY (US)

(72) Inventors: Timothy H. Bestor, New York, NY (US); John R. Edwards, St. Louis, MO (US); Jingyue Ju, Englewood Cliffs, NJ (US); Xiaoxu Li, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/578,125

(22) Filed: Dec. 19, 2014

(65) Prior Publication Data
US 2015/0148240 A1    May 28, 2015

Related U.S. Application Data

(62) Division of application No. 13/055,208, filed as application No. PCT/US2009/004257 on Jul. 22, 2009, now abandoned.

(60) Provisional application No. 61/135,714, filed on Jul. 22, 2008.

(51) Int. Cl.
    *C12Q 1/68*       (2006.01)
    *C12P 19/34*     (2006.01)
    *C07H 19/23*     (2006.01)

(52) U.S. Cl.
    CPC .......... *C12Q 1/6806* (2013.01); *C07H 19/23* (2013.01); *C12Q 1/6827* (2013.01); *C12Q 1/6874* (2013.01)

(58) Field of Classification Search
    CPC ..................................................... C12Q 1/6806
    USPC ....................................... 435/6.1, 91.1, 91.2
    See application file for complete search history.

(56) References Cited

U.S. PATENT DOCUMENTS

| | | | |
|---|---|---|---|
| 5,032,594 | A | 7/1991 | Takehiko et al. |
| 5,824,669 | A | 10/1998 | Garvey et al. |
| 6,046,329 | A | 4/2000 | Prusse et al. |
| 2006/0019270 | A1 | 1/2006 | Yang et al. |
| 2006/0172988 | A1 | 8/2006 | Johansson et al. |
| 2007/0161007 | A1 | 7/2007 | Rajski et al. |
| 2011/0177508 | A1 | 7/2011 | Bestor et al. |

FOREIGN PATENT DOCUMENTS

| | | |
|---|---|---|
| EP | 1 712 557 A1 | 10/2006 |
| WO | WO 2005/121361 A2 | 12/2005 |

OTHER PUBLICATIONS

International Search Report issued by the International Searching Authority (ISA/US) on Sep. 16, 2009 in connection with PCT International Application No. PCT/US2009/004257.

(Continued)

*Primary Examiner* — Jezia Riley
(74) *Attorney, Agent, or Firm* — John P. White; Cooper & Dunham LLP

(57) ABSTRACT

This invention provides methods of derivatizing a double-stranded DNA comprising contacting double-stranded DNA with a CpG methyltransferase and an s-adenosylmethionine analog. This invention also provides methods of sequencing DNA to determine methylation patterns.

10 Claims, 20 Drawing Sheets

(56) References Cited

OTHER PUBLICATIONS

Written Opinion of the International Searching Authority issued by the International Searching Authority (ISA/US) on Sep. 16, 2009 in connection with PCT International Application No. PCT/US2009/004257.
Grunau et al. Bisulfite genomic sequencing: a systematic investigation of critical experimental parameters. Nucleic Acid Research, 2001, vol. 29, No. 13 e65 [Abstract].
PubChem Compound Summary for CID446104, available online at <http://pubchem.ncbi.nlm.nih.gov/summary/summary.cgi?loc=ec_rcs&cid=446104> (Jun. 24, 2005). Retrieved Sep. 1, 2009.
PCT International Application Publication No. WO 03/031648 A2 (Epigenomics AG [DE]; Berlin Kurt [DE]) published Apr. 17, 2003.
Extended European Search Report issued Mar. 4, 2012 in connection with European Patent Application No. 09800674.5.
Dalhoff C et al. (2006a) Direct transfer of extended groups from synthetic cofactors by DNA methyltransferases. *Nat. Chem. Biol.* 2:31-32.
Dalhoff C et al. (2006b) Synthesis of S-adenosyl-L methionine analogs and their use for sequence-specific transkylation of DNA by methyltransferases. *Nat. Protoc.* 1, 1879-86.
Lukinavic G et al. Targeted labeling of DNA by Methyltransferase-Directed Transfer of Activated Groups (mTAG). Journal of the American Chemical Society. 129, 10 (2007) 2758-2759.
Communication pursuant to Article 94(3) EPC issued Sep. 1, 2013 in connection with European Patent Application No. 09800674.5.
Invitation pursuant to Article 94(3) and Rule 71(1) EPC issued Apr. 24, 2014 in connection with European Patent Application No. 09800674.5.
First Office Action issued in Mar. 4, 2013 in connection with Chinese Patent Application No. 200980129203.8, filed Jul. 22, 2009.
Second Office Action issued in Jan. 1, 2014 in connection with Chinese Patent Application No. 200980129203.8, filed Jul. 22, 2009.
Third Office Action issued in Oct. 20, 2014 in connection with Chinese Patent Application No. 200980129203.8, filed Jul. 22, 2009.
Office Action issued Jan. 7, 2014 in connection with U.S. Appl. No. 13/055,208, filed Apr. 8, 2011.
Office Action issued Jan. 15, 2014 in connection with U.S. Appl. No. 13/055,208, filed Apr. 8, 2011.
Office Action issued Jun. 24, 2014 in connection with U.S. Serial No. 13/055,208, filed Apr. 8, 2011.
Molecular Genetics, Yehua Yang, p. 61-64, China Agricultural Press, Mar. 31, 2001.
Fourth Office Action issued Feb. 9, 2015 in connection with Chinese Patent Application No. 200980129203.8 (including English Language Translation).

UNIVERSAL METHYLATION PROFILING METHODS

This application is a divisional of U.S. Ser. No. 13/055,208, filed Apr. 8, 2011, which is a §371 national stage of PCT International Application No. PCT/US2009/004257, filed Jul. 22, 2009, which claims the benefit of U.S. Provisional Application No. 61/135,714, filed Jul. 22, 2008, the entire contents of each of which are hereby incorporated by reference into the subject application.

Throughout this application, various publications are referenced in parentheses. Full citations for these references may be found at the end of the specification immediately preceding the claims. The disclosures of these publications in their entireties are hereby incorporated by reference into this application to more fully describe the state of the art to which this invention pertains.

BACKGROUND OF THE INVENTION

The mammalian genome contains ~28 million CpG sites, about 60% of which are methylated at the 5 position of the cytosine (Rollins et al., 2006). Methylation of relatively CpG-rich promoters causes very strong transcriptional repression (Stein et al., 1982, Lorincz et al., 2002); promoter methylation is largely restricted to imprinted genes, transposon promoters, and to CpG islands on the inactive X chromosome. Many experiments have demonstrated faithful inheritance of methylation patterns over many cell divisions in somatic cells (Wigler et al., 1981; Lorincz et al., 2002) and over many sexual generations in plants, which contain a DNA methylating system similar to that of vertebrates (reviewed by Goll and Bestor, 2005). This heritability means that genomic methylation patterns could have many biological functions, and many such functions have been proposed. The most familiar of these is gene control during development (Holliday and Pugh, 1975; Riggs, 1975). Other proposed functions include genome stability (Chen at al., 1996) learning and memory (Miller and Sweatt, 2007; this claim is highly controversial), defense against transposons (Yoder at al., 1997; Bestor, 2003), and X chromosome inactivation (Panning and Jaenisch, 1996). While much controversy remains, the ability of promoter methylation to silence transcription and the heritability of genomic methylation patterns are supported by a large and compelling body of evidence.

Null mutations in any of the three DNA methyltransferases are recessive lethals, and loss of DNMT3L causes male sterility and maternal effect lethality in females. Mutations in the DNA methyltransferase gene DNMT3B cause ICE syndrome, which is characterized by a combined immunodeficiency usually fatal in childhood, very unstable centromeres of chromosomes 1, 9, and 16, and mild but characteristic facial anomalies (Xu at al., 1999). Partial demethylation or hypermethylation in mutant mice lead to abnormal expression of imprinted genes with early lethality (Biniszkiewicz 2002; Yamada at al., 2005). While the normal function of the mammalian genome clearly depends on genomic methylation patterns, the abnormalities of genomic methylation patterns found in human disease have been difficult to discern because of the lack of methods for the methylation profiling of the entire genome.

SUMMARY OF THE INVENTION

A compound is provided having the structure:

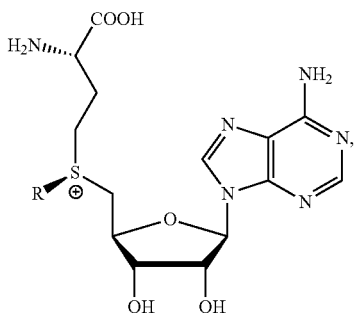

wherein R is

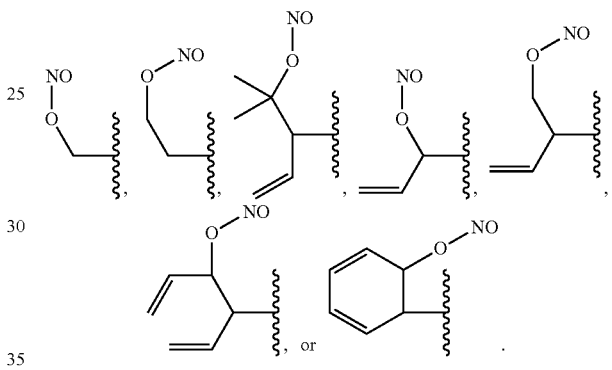

A composition of matter is provided comprising a compound having the structure:

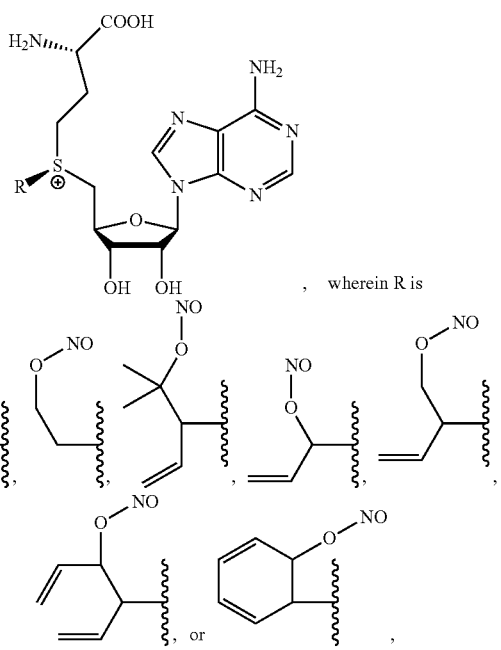

attached to a CpG methyltransferase.

A process is provided of producing a derivative of a double-stranded DNA comprising contacting the double-stranded DNA with a CpG methyltransferase and an s-adenosylmethionine analog having the structure:

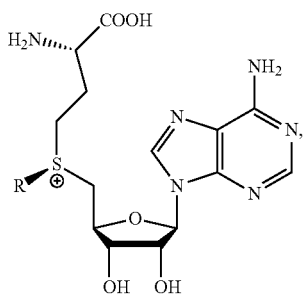

wherein R is a chemical group capable of being transferred from the s-adenosylmethionine analog by the CpG methyltransferase to a 5-carbon of a non-methylated cytosine of the double-stranded DNA, under conditions such that the chemical group covalently binds to the 5-carbon of the non-methylated cytosine of the double-stranded DNA, and thereby produces the derivative of the double-stranded DNA.

A method is provided of determining whether a cytosine present within a double-stranded DNA sequence of known sequence is non-methylated comprising:
  producing a derivative of the double-stranded DNA by contacting the double-stranded DNA with a CpG methyltransferase and an s-adenosylmethionine analog having the structure:

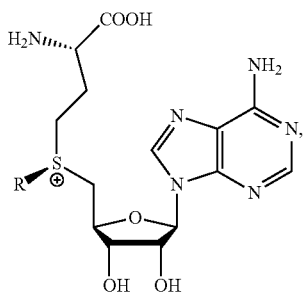

wherein R is a chemical group capable of being transferred from the s-adenosylmethionine analog by the CpG methyltransferase to a 5 carbon of a non-methylated cytosine of the double-stranded DNA so as to covalently bond the chemical group to the 5 carbon of the non-methylated cytosine of the double-stranded DNA, thereby making a derivatized double stranded DNA;
separately obtaining a single strand of the derivatize of the double-stranded DNA;
sequencing the single strand so obtained; and
comparing the sequence of the single strand determined in step c) to the sequence of a corresponding strand of the double-stranded DNA of which a derivative has not been produced,
wherein the presence of a thymidine analog in the single strand of the derivative instead of a cytosine at a predefined position in the corresponding strand of the double-stranded DNA of which a derivative has not been produced indicates that the cytosine at that position in the double-stranded DNA is non-methylated.

A derivatized DNA molecule is provided, wherein the derivatized DNA molecule differs from DNA by comprising nucleotide residue comprising a base having the following structure:

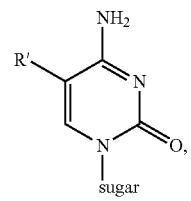

wherein R' is

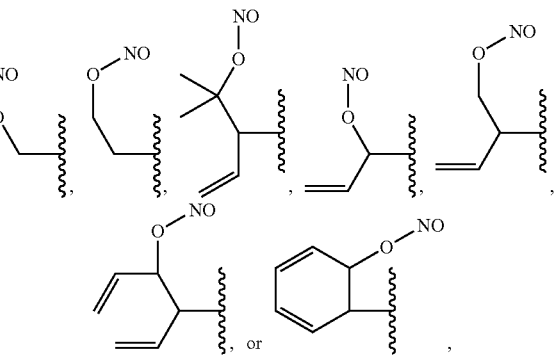

and wherein the sugar is a sugar of the nucleotide residue.

A derivatized DNA molecule is provided, wherein the derivatized DNA molecule differs from DNA by comprising a nucleotide residue comprising a base having the following structure:

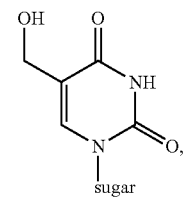

wherein the sugar is a sugar of the nucleotide residue.

A compound is provided having the structure:

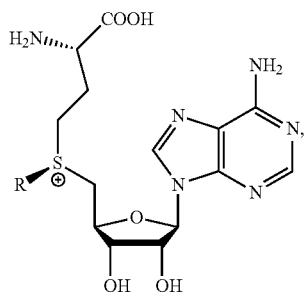

wherein R is

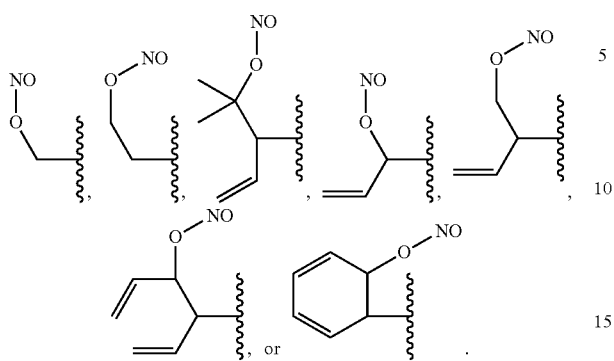

A method is provided of derivatizing a double-stranded DNA comprising contacting double-stranded DNA with a CpG methyltransferase and an s-adenosylmethionine analog having the structure:

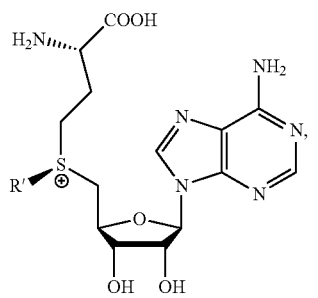

wherein R' is a chemical group capable of being transferred from the s-adenosylmethionine analog by the CpG methyltransferase to a 5 carbon of a non-methylated cytosine of the double-stranded DNA, so as to covalently bond the chemical group to the 5 carbon of the non-methylated cytosine of the double-stranded DNA under conditions permitting the formation of a six-membered ring joining the 4 and 5 carbons of the non-methylated cytosine, thereby derivatizing the double-stranded DNA.

A method is provided of determining whether a cytosine, in a DNA sequence of known sequence, is non-methylated comprising:

derivatizing a double-stranded DNA of known sequence by contacting double-stranded DNA with a CpG methyltransferase and an s-adenosylmethionine analog having the structure:

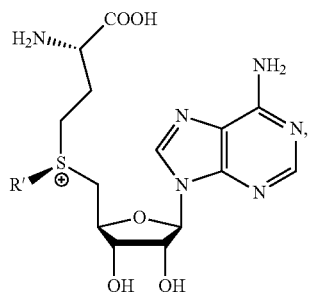

wherein R is a chemical group capable of being transferred from the s-adenosylmethionine analog by the CpG methyltransferase to a 5 carbon of a non-methylated cytosine of the double-stranded DNA, so as to covalently bond the chemical group to the 5 carbon of the non-methylated cytosine of the double-stranded DNA under conditions permitting the formation of a neobase which comprises a six-membered ring joining the 4 and 5 carbons of the non-methylated cytosine, thereby derivatizing the double-stranded DNA;

obtaining a single strand of the derivatized double-stranded DNA;

sequencing the single strand; and comparing the sequence of the single strand determined in step c) to sequence of a strand of the double-stranded DNA of known sequence, wherein a neobase identified in the single strand in place of a cytosine at the corresponding residue position in the strand of the double-stranded DNA of known sequence indicates that the cytosine at that residue position in the double-stranded DNA of known sequence is non-methylated.

A kit is provided for derivatizing a double-stranded DNA molecule comprising:

a) a compound having the structure:

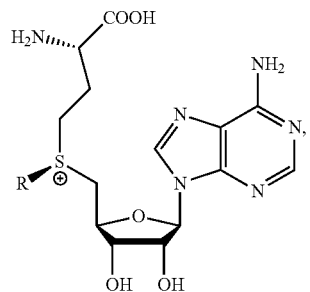

wherein R is

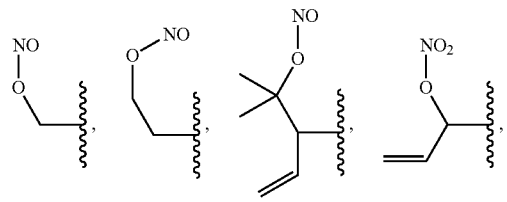

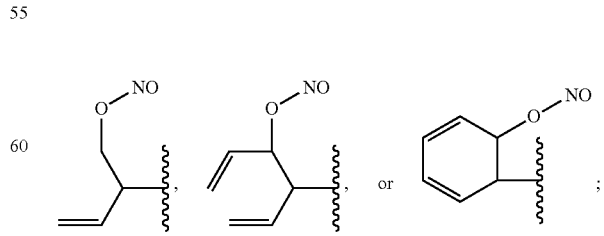

b) a CpG methyltransferase; and c) instructions for use.

A kit is provided comprising a cofactor for a SssI methyltransferase enzyme comprising:
a) a compound having the structure:

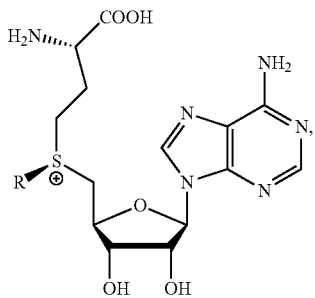

wherein R is

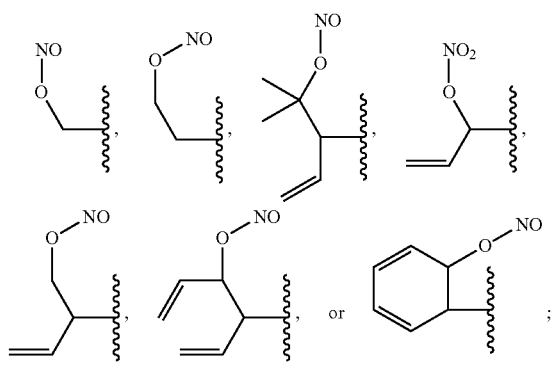

and
b) instructions for use.

A compound is provided having the structure:

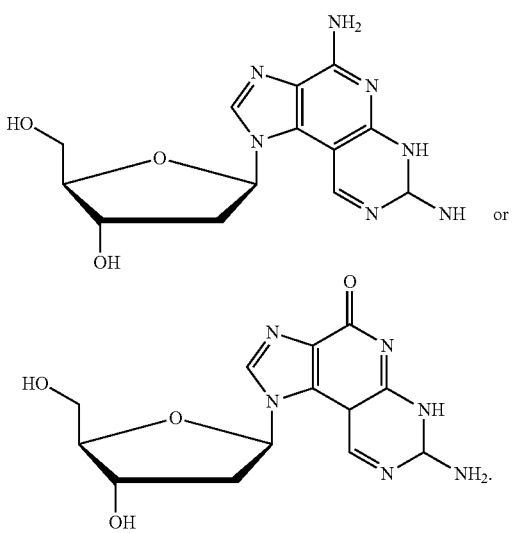

BRIEF DESCRIPTION OF THE FIGURES

FIG. 18c shows that methylation status across multiple sequence compartments is very similar between unrelated individuals.

DETAILED DESCRIPTION OF THE INVENTION

Terms

Figure 1:
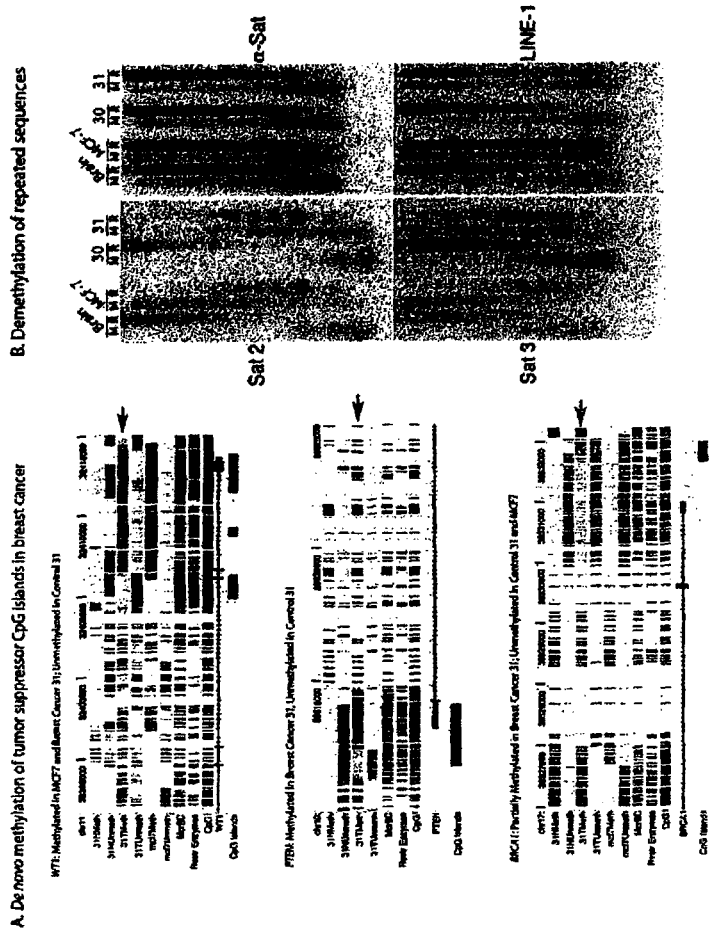
FIG. 1. Methylation abnormalities in breast cancer: gains and losses of DNA methylation in different sequence compartments. (a) Results are shown of the method developed by Rollins et al (2006) to fractionate DNA by methylation status was coupled to ABI SOLiD ultra-high throughput DNA sequencing to determine the methylation status of ~70% of the CpG dinucleotides in the entire genome in DNA from an invasive ductal carcinoma (31T), normal breast tissue from the same patient (31N), and the MCF7 breast cancer cell line. (b) Demethylation of Satellite 2 and 3 and LINE-1 promoters in breast carcinoma are shown.

As used herein, and unless stated otherwise, each of the following terms shall have the definition set forth below.

A Adenine;
C—Cytosine;
DNA—Deoxyribonucleic acid;
G—Guanine;
RNA—Ribonucleic acid;
T—Thymine; and
U—Uracil.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Type" of nucleotide refers to A, G, C, T or U. "Type" of base refers to adenine, guanine, cytosine, uracil or thymine.

"Mass tag" shall mean a molecular entity of a predetermined size which is capable of being attached by a cleavable bond to another entity.

"Solid substrate" shall mean any suitable medium present in the solid phase to which a nucleic acid or an agent may be affixed. Non-limiting examples include chips, beads and columns.

"Hybridize" shall mean the annealing of one single-stranded nucleic acid to another nucleic acid based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.)

EMBODIMENTS OF THE INVENTION

A compound is provided having the structure:

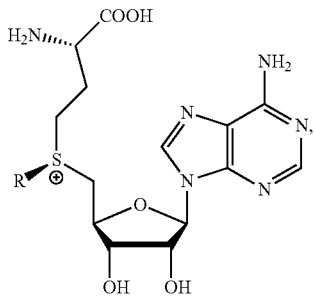

wherein R is

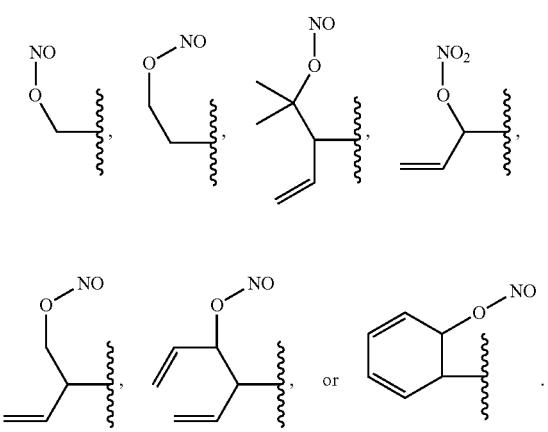

In an embodiment of the compound R is

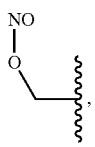

A composition of matter is provided comprising a compound having the structure:

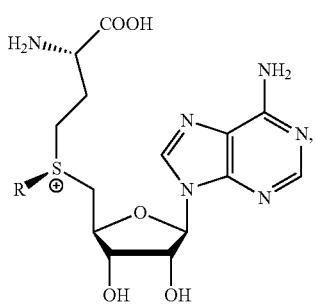

wherein R is

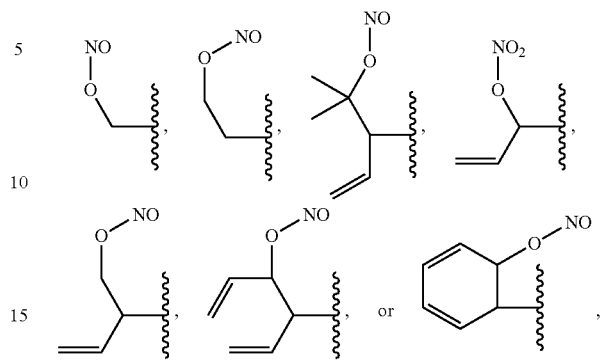

attached to a CpG methyltransferase.

In an embodiment the compound is attached to the active site of the CpG methyltransferase.

In an embodiment the CpG methyltransferase is SssI methyltransferase.

A process is provided of producing a derivative of a double-stranded DNA comprising contacting the double-stranded DNA with a CpG methyltransferase and an s-adenosylmethionine analog having the structure:

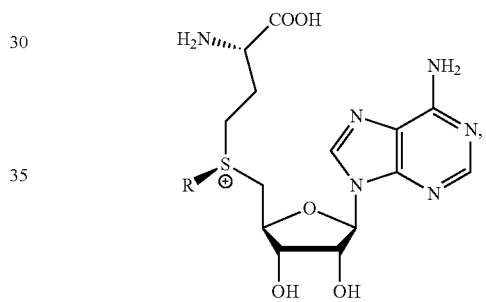

wherein R is a chemical group capable of being transferred from the s-adenosylmethionine analog by the CpG methyltransferase to a 5-carbon of a non-methylated cytosine of the double-stranded DNA, under conditions such that the chemical group covalently binds to the 5-carbon of the non-methylated cytosine of the double-stranded DNA, and thereby produces the derivative of the double-stranded DNA.

In an embodiment of the process the chemical group has the structure:

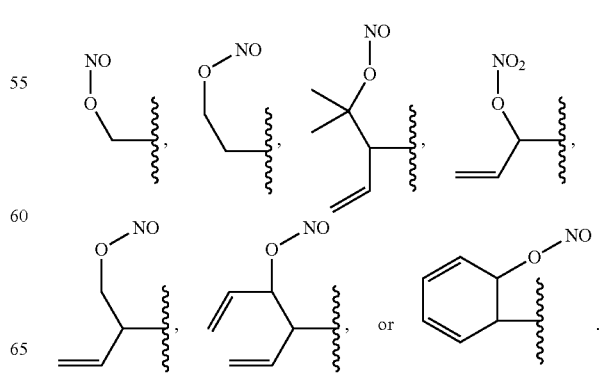

in an embodiment of the processes described above the chemical group has the structure:

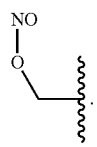

In an embodiment of the processes described above the CpG methyltransferase is SssI methyltransferase.

In an embodiment of the processes described above the chemical group capable of being transferred from the s-adenosylmethionine analog by the CpG methyltransferase to the 5-carbon of the non-methylated cytosine of the double-stranded DNA permits oxidative deamination of a 4-position of the non-methylated cytosine when it is covalently bound to the 5-carbon of the non-methylated cytosine of the double-stranded DNA.

In an embodiment of the processes described above the non-methylated cytosine is immediately adjacent in sequence to a guanine in a single strand of the double-stranded DNA.

A method is provided of determining whether a cytosine present within a double-stranded DNA sequence of known sequence is non-methylated comprising:
  producing a derivative of the double-stranded DNA by contacting the double-stranded DNA with a CpG methyltransferase and an s-adenosylmethionine analog having the structure:

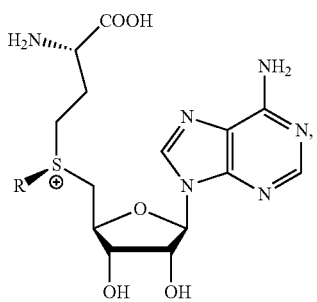

wherein R is a chemical group capable of being transferred from the s-adenosylmethionine analog by the CpG methyltransferase to a 5 carbon of a non-methylated cytosine of the double-stranded DNA so as to covalently bond the chemical group to the 5 carbon of the non-methylated cytosine of the double-stranded DNA, thereby making a derivatized double stranded DNA;
  separately obtaining a single strand of the derivatize of the double-stranded DNA;
  sequencing the single strand so obtained; and
  comparing the sequence of the single strand determined in step c) to the sequence of a corresponding strand of the double-stranded DNA of which a derivative has not been produced,
  wherein the presence of a thymidine analog in the single strand of the derivative instead of a cytosine at a predefined position in the corresponding strand of the double-stranded DNA of which a derivative has not been produced indicates that the cytosine at that position in the double-stranded DNA is non-methylated.

In an embodiment of the method described above the chemical group has the structure:

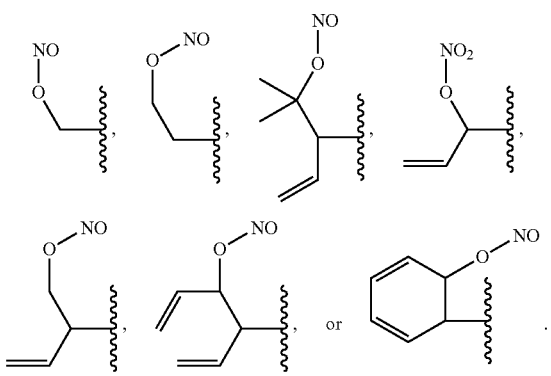

In an embodiment of the methods described above the chemical group has the structure:

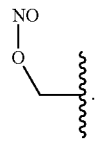

In an embodiment of the methods described above the CpG methyltransferase is SssI methyltransferase.

In an embodiment of the methods described above the non-methylated cytosine is immediately adjacent in sequence to a guanine in a single strand of the double-stranded DNA.

In an embodiment of the methods described above the chemical group capable of being transferred from the s-adenosylmethionine analog by the CpG methyltransferase to the 5 carbon of the non-methylated cytosine of the double-stranded DNA permits oxidative deamination of a 4 position of the non-methylated cytosine when it is covalently bound to the 5 carbon of the non-methylated cytosine of the double-stranded DNA.

In an embodiment of the methods described above in step 0 the sequencing is sequencing by synthesis.

In an embodiment of the methods described above the sequencing by synthesis comprises contacting the derivatized single strand with a DNA polymerase, a primer oligonucleotide, dATP, dCTP, dGTP, dTTP, and a dideoxynucleotide triphosphate having a detectable label attached thereto.

In an embodiment of the methods described above the detectable label is radioactive or fluorescent.

In an embodiment of the methods described above the detectable label is a mass tag.

In an embodiment of the methods described above the method further comprising attaching the single strand to a solid support prior to step c).

A derivatized DNA molecule is provided, wherein the derivatized DNA molecule differs from DNA by comprising a nucleotide residue comprising a base having the following structure:

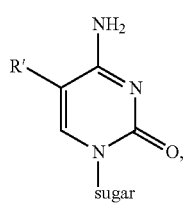

wherein R' is

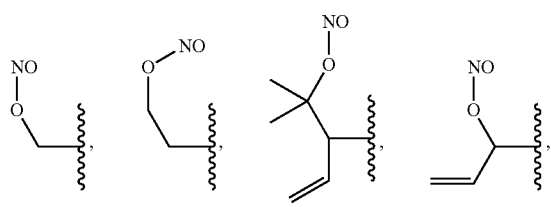

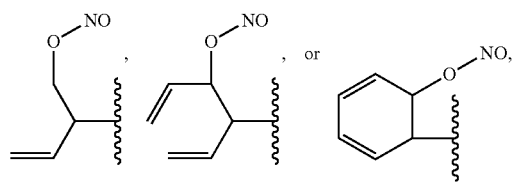

and wherein the sugar is a sugar of the nucleotide residue.

A derivatized DNA molecule is provided, wherein the derivatized DNA molecule differs from DNA by comprising a nucleotide residue comprising a base having the following structure:

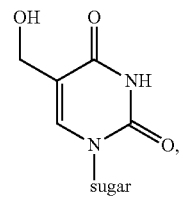

wherein the sugar is a sugar of the nucleotide residue.

A compound is provided having the structure:

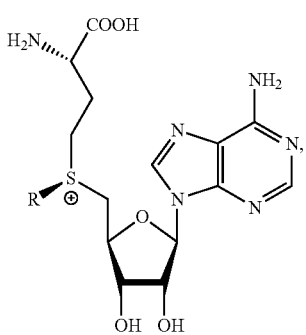

wherein R is

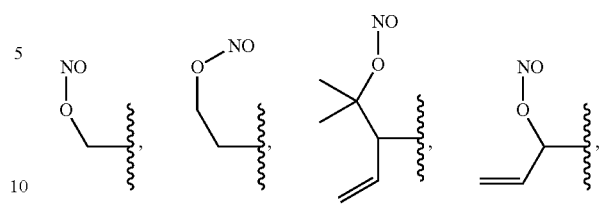

In an embodiment of the compounds described above R is

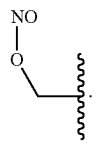

A method is provided of derivatizing a double-stranded DNA comprising contacting double-stranded DNA with a CpG methyltransferase and an s-adenosylmethionine analog having the structure:

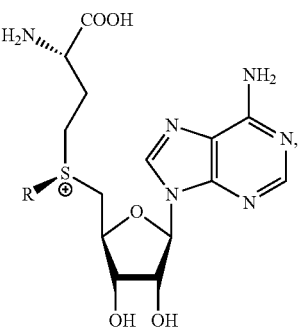

wherein R' is a chemical group capable of being transferred from the s-adenosylmethionine analog by the CpG methyltransferase to a 5 carbon of a non-methylated cytosine of the double-stranded DNA, so as to covalently bond the chemical group to the 5 carbon of the non-methylated cytosine of the double-stranded DNA under conditions permitting the formation of a six-membered ring joining the 4 and 5 carbons of the non-methylated cytosine, thereby derivatizing the double-stranded DNA.

In an embodiment of the methods described above the chemical group has the structure:

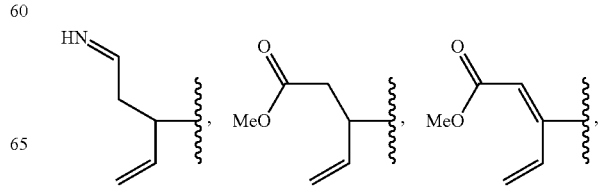

-continued

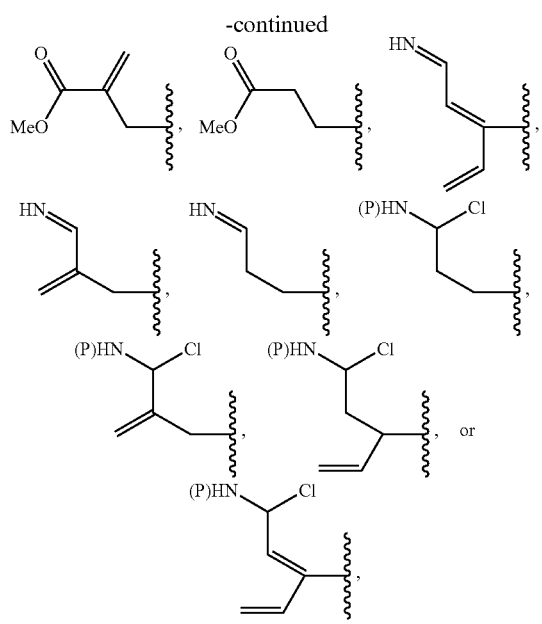

In an embodiment of the methods described above the CpG methyltransferase is SssI methyltransferase.

A method is provided of determining whether a cytosine, in a DNA sequence of known sequence, is non-methylated comprising:

derivatizing a double-stranded DNA of known sequence by contacting double-stranded DNA with a CpG methyltransferase and an s-adenosylmethionine analog having the structure:

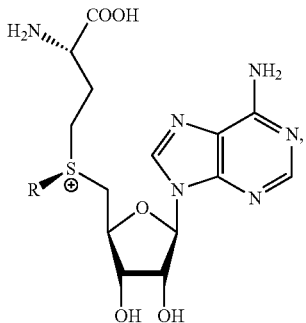

wherein R' is a chemical group capable of being transferred from the s-adenosylmethionine analog by the CpG methyltransferase to a 5 carbon of a non-methylated cytosine of the double-stranded DNA, so as to covalently bond the chemical group to the 5 carbon of the non-methylated cytosine of the double-stranded DNA under conditions permitting the formation of a neobase which comprises a six-membered ring joining the 4 and 5 carbons of the non-methylated cytosine, thereby derivatizing the double-stranded DNA;

obtaining a single strand of the derivatized double-stranded DNA;

sequencing the single strand; and comparing the sequence of the single strand determined in step c) to sequence of a strand of the double-stranded DNA of known sequence, wherein a neobase identified in the single strand in place of a cytosine at the corresponding residue position in the strand of the double-stranded DNA of known sequence indicates that the cytosine at that residue position in the double-stranded DNA of known sequence is non-methylated.

In an embodiment of the methods described above the chemical group has the structure:

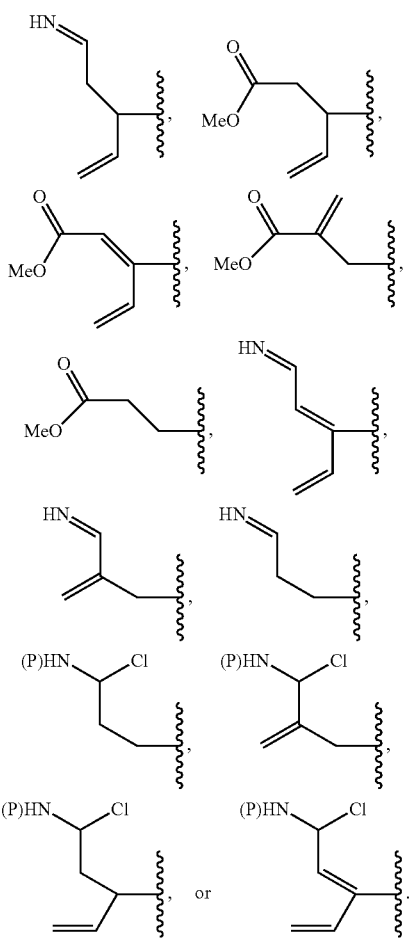

In an embodiment of the methods described above the CpG methyltransferase is SssI methyltransferase.

In an embodiment of the methods described above in step c) the sequencing is sequencing by synthesis.

In an embodiment of the methods described above the sequencing by synthesis comprises contacting the derivatized single strand with a DNA polymerase, a primer oligonucleotide, dATP, dCTP, dGTP, dTTP, neobase y or neobase Y' and a dideoxynucleotide triphosphate having a detectable label attached thereto.

In an embodiment of the methods described above the detectable label is radioactive or fluorescent.

In an embodiment of the methods described above the detectable label is a mass tag.

In an embodiment of the methods described above, the method further comprises attaching the derivatized single strand to a solid support prior to step c).

A kit is provided for derivatizing a double-stranded DNA molecule comprising:

a) a compound having the structure:

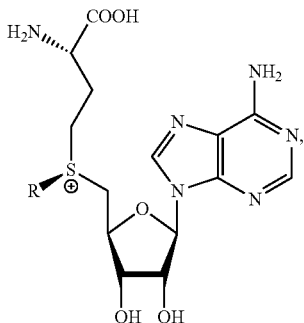

wherein R is

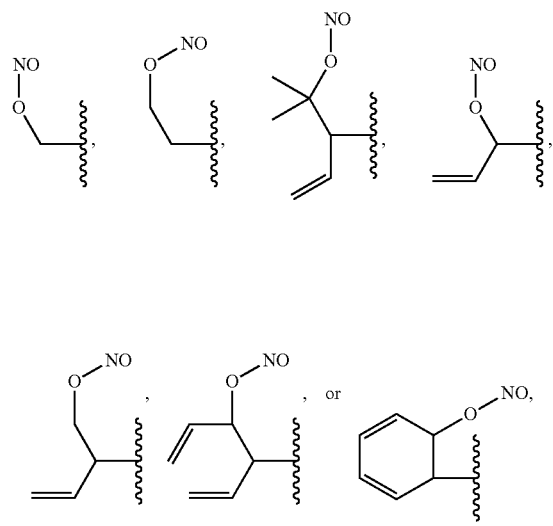

b) a CpG methyltransferase; and
c) instructions for use.

In an embodiment of the kit the CpG methyltransferase is SssI methyltransferase.

A kit is provided comprising a cofactor for a SssI methyltransferase enzyme comprising:

a) a compound having the structure:

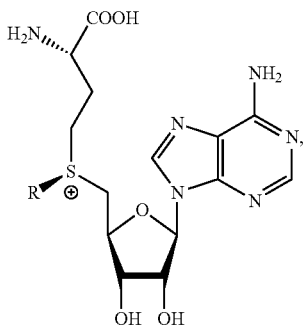

wherein R is

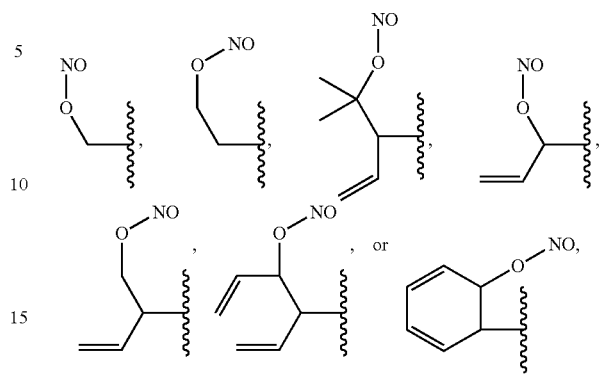

and
b) instructions for use.

A compound is provided having the structure:

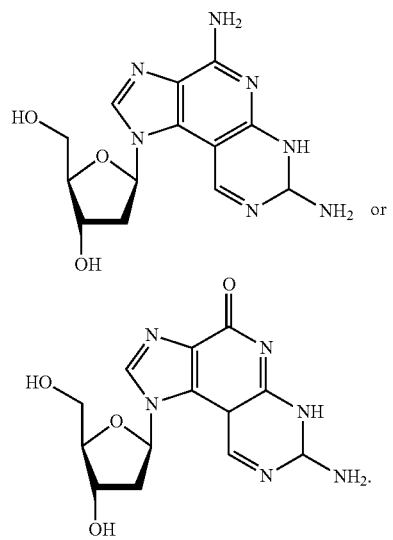

This invention provides the instant methods and processes, wherein the detectable label bound to the base via a cleavable linker is a dye, a fluorophore, a chromophore, a combinatorial fluorescence energy transfer tag, a mass tag, or an electrophore. Combinatorial fluorescence energy tags and methods for production thereof are disclosed in U.S. Pat. No. 6,627,748, which is hereby incorporated by reference.

Detectable tags and methods of affixing nucleic acids to surfaces which can be used in embodiments of the methods described herein are disclosed in U.S. Pat. Nos. 6,664,079 and 7,074,597 which are hereby incorporated by reference.

This invention also provides the instant methods and processes, wherein the DNA is bound to a solid substrate. This invention also provides the instant method, wherein the DNA is bound to the solid substrate via 1,3-dipolar azide-alkyne cycloaddition chemistry. This invention also provides the instant methods and processes, wherein the DNA is bound to the solid substrate via a polyethylene glycol molecule. This invention also provides the instant methods and processes, wherein the DNA is alkyne-labeled. This invention also provides the instant method and processes, wherein the DNA is bound to the solid substrate via a polyethylene glycol molecule and the solid substrate is azide-functionalized. This invention also provides the instant methods and processes, wherein the DNA is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. This invention also provides the instant methods and processes, wherein the DNA is bound to the solid substrate via a polyethylene glycol molecule and the solid substrate is azide-functionalized or the DNA is immobilized on the solid substrate via an azido linkage, an alkynyl linkage, or biotin-streptavidin interaction. In an embodiment, the DNA or nucleic acid is attached/bound to the solid surface by covalent site-specific coupling chemistry compatible with DNA.

This invention also provides the instant methods and processes, wherein the solid substrate is in the form of a chip, a bead, a well, a capillary tube, a slide, a wafer, a filter, a fiber, a porous media, or a column. This invention also provides the instant methods and processes, wherein the solid substrate is gold, quartz, silica, plastic, glass, nylon, diamond, silver, metal, or polypropylene. This invention also provides the instant method, wherein the solid substrate is porous. Chips or beads may be made from materials common for DNA microarrays, for example glass or nylon. Beads/midro-beads may be in turn immobilized to chips.

This invention also provides the instant methods and processes, wherein about 1000 or fewer copies of the DNA are bound to the solid substrate. This invention also provides the instant methods and processes wherein $2 \times 10^7$, $1 \times 10^7$, $1 \times 10^6$ or $1 \times 10^4$ or fewer copies of the DNA are bound to the solid substrate.

This invention also provides the instant methods and processes, wherein the nucleotide analogues comprise one of the fluorophores Cy5, Bodipy-FL-510, ROX and R6G.

This invention also provides the instant methods and processes, wherein the DNA polymerase is a 9° N polymerase or a variant thereof. DNA polymerases which can be used in the instant invention include, for example E. Coli DNA polymerase I, Bacteriophage T4 DNA polymerase, Sequenase™, Taq DNA polymerase and 9° N polymerase (exo-) A485L/Y409V. RNA polymerases which can be used in the instant invention include, for example, Bacteriophage SP6, T7 and T3 RNA polymerases.

Methods for production of cleavably capped and/or cleavably linked nucleotide analogues are disclosed in U.S. Pat. No. 6,664,079, which is hereby incorporated by reference.

DNA Methylation is described in U.S. Patent Application Publication No. 2003-0232371 A1 which is hereby incorporated by reference in its entirety.

All combinations and subcombinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

DNA methylation at specific sequences was first analyzed by southern blotting after cleavage with methylation-sensitive restriction endonucleases (MSREs) such as HpaII, which fails to cleave the sequence 5'-CCGG-3' when the central CpG dinucleotide is methylated (Waalwijk and Flavell, 1978). This method is robust and provides an internal control for complete digestion when the blot is reprobed for mitochondrial DNA, which is not methylated and is present in many copies. However, the MSRE method is tedious, expensive, requires relatively large amounts of radioactive nucleotides, and can test only a small number of CpG sites per fragment because only ~20% of all CpG sites fall within the recognition sequence of a known MSRE. If a given fragment contains many CpG sites and only one or a few are unmethylated, the sequence is often scored as unmethylated. MSRE provides the best-controlled method of methylation analysis, but low throughput and other shortcomings means that it cannot form the basis for a whole-genome methylation profiling platform.

Numerous other PCR-based methods for rapid methylation profiling of single or small numbers of CpG sites have been developed; examples are methylation-sensitive PCR (MSP; Steigerwald et al., 1990), COBRA (Eads and Laird, 2002) and methyl-light (Trinh et al., 2001). These methods are fast and inexpensive but can test only small numbers of CpG sites; they are unsuitable for unbiased whole-genome methylation profiling. After specific methylation abnormalities have been found to be associated with a given disorder, these focused methods might be found to be appropriate for diagnostic and prognostic tests in clinical samples.

Microarray analysis has been applied, with considerable success (i.e., Gitan et al., 2002). However, microarray methods cannot address the methylation status of repeated sequences (which contain the majority of 5-methylcytosine in the genome; Rollins et al., 2006), and CpG islands give rise to high noise levels as a result of their high G+C contents. Microarrays cannot examine the methylation status of each CpG dinucleotide. Again, while this method has its advantages, it is not suited to whole-genome methylation profiling.

An important advance in methylation profiling came with the introduction of bisulfite genomic sequencing (BGS) by Susan Clark and Marianne Frommer in 1994 (Clark at al., 1994). BGS depends on the ability of sodium bisulfite to oxidatively deaminate the 4 position of cytosine, thereby converting the base to uracil. A methyl group at the 5 position prevents bisulfite from adding across the 5-6 double bond, which renders 5-methyl cytosine resistant to bisulfite conversion. PCR amplification followed by DNA sequencing produces a C lane in which each band corresponds to what was a 5-methylcytosine in the starting DNA; all unmethylated cytosines are sequenced as thymines. BGS was an important advance over earlier methods of genomic sequencing (Church and Gilbert, 1984).

However, BGS has severe drawbacks when applied to whole genome methylation profiling. First, it cannot be known if the thymines in the final sequence were thymines or cytosines in the starting material. This severely reduces the information content of DNA. As a result, the new ultrahigh throughput DNA sequencing methods cannot be used, as sequence reeds are short and a large percentage of the sequences cannot be mapped to a single position in the genome. Very few repetitive sequences can be mapped at all. BGS is largely restricted to pre-selected regions of the genome where primers can be designed to selectively amplify the region of interest. Whole-genome methylation profiles cannot be obtained by this method, as many regions of the genome do not allow design of unique primer sets. CpG islands are especially problematic, as primer sites free of CpG dinucleotides cannot be found in most CpG islands. Second, bisulfite conversion requires that the DNA be single stranded; any double stranded DNA will be resistant to conversion and will be scored as methylated. As a result, bisulfite treatment must be performed under very harsh conditions (0.2 N sodium hydroxide at elevated temperature for several hours). Under these conditions bisulfite conversion and chain breakage are competing reactions, and bisulfite conversion only approaches completion when >95% of the DNA has been cleaved to less than 350 bp (Warnecke at al., 2002). This means that large amounts of starting DNA must be used and the DNA must be long. This prevents the use of DNA from paraffin sections, where the DNA is almost all <300 bp, and also prevents the use of small amounts of DNA, as in the case of early embryos, small tissue biopsies, and other cases in which large amounts of DNA are not available. Third. CpG dinucleotides in certain sequence contexts are inherently resistant to bisulfite conversion (Warnecke et al., 2002), and are scored as spurious sites of methylation. Fourth, the loss of all C-G base pairs introduces a large bias in the PCR amplification step in favor of PCR product derived from unconverted or methylated starting material. (Warnecke at al., 1997). Each of these artifacts can be severe.

Together the loss of sequence information upon bisulfite conversion, the strong PCR biases, the artifacts of bisulfite conversion, and the need for large amounts of long starting DNA renders conventional BGS inappropriate for whole-genome methylation profiling by ultrahigh throughput DNA sequencing.

Over the past few years this laboratory has developed new methods to fractionate the normal human genome into methylated and unmethylated compartments and have determined the methylation status of CpG dinucleotides in excess of 30 million base pairs from the fractionated genomes in order to characterize the methylation landscape of the normal human genome (Rollins et al., 2006). In that work, new computational methods were developed that mapped annotated features of the genome onto very large assemblages of sequence data. Although this method, which depends on the enzymatic fractionation of DNA into methylated and unmethylated compartments, has provided information on the methylation status of more CpG sites than the sum total of all other methods, it remains incapable of whole-genome methylation profiling because of shortcomings that cannot be overcome with existing technology.

Examples of methylation abnormalities are identified by the method of Rollins at al. (2006). It should be noted that the method disclosed herein can be applied to any sequenced genome; mammary carcinoma is shown because highly abnormal methylation patterns are known to be present in the genomes of these cells and these genomes provide an excellent test system.

FIG. 1 shows methylation abnormalities in breast cancer: gains and losses of DNA methylation in different sequence compartments. In FIG. 1A results are shown of the method developed by Rollins at al (2006) to fractionate DNA by methylation status was coupled to ABI SOLID ultra-high throughput DNA sequencing to determine the methylation status of ~70% of the CpG dinucleotides in the entire genome in DNA from an invasive ductal carcinoma (31T), normal breast tissue from the same patient (31N), and the MCF7 breast cancer cell line. Cleavage sites for the methylation-dependent McrBC enzyme complex are shown as a single track, as are cleavage sites for the set of 6 methylation-sensitive restriction endonucleases. The locations of all CpG sites in the area of interest are shown in the track above the diagram of the relevant genes. The arrows at right indicate de novo methylation specific to CpG islands in the carcinoma. Note that the CpG islands associated with the 5' ends of the WT1 and PTEN genes are methylated in 31T and MCF7 but not in normal breast tissue, while the BRCA1 CpG island is partially methylated in the carcinoma but unmethylated in both normal breast tissue and in the MCF7 cell line. FIG. 1B shows demethylation of Satellite 2 and 3 and LINE-1 promoters in breast carcinoma. DNA from the sources listed at top were digested with McrBC (M) or the battery of MSREs (R), and then subjected to southern blot with the probes indicated at the sides of the autoradiograms. Dense methylation sensitizes to McrBC and renders the DNA resistant to MSREs, as in the case of normal brain DNA in lanes 1 and 2. Both MCF7 and carcinoma 31 can be seen to be severely demethylated at satellites 2 and 3 and at LINE-1 transposon promoters. The same hybridization membrane was repeatedly stripped and reprobed; alpha satellite DNA is heavily methylated in all cases and provides an internal control for complete digestion. Tumor 30 does not show evidence of demethylation of repeated sequences; whole-genome methylation profiling of this tumor and adjacent normal tissue from the same patient is currently underway. Tissue samples were provided by Dr. H. Hibshoosh (Department of Pathology, Columbia) and were used under an IRB-approved protocol. Custom tracks for the UCSB browser views in A were written by J. Edwards. SOLiD sequencing was performed by Applied Biosystems. Inc. Methylation analysis was not targeted to the regions shown in A above—yet this degree of coverage was obtained for the entire annotated genome in one SOLiD run.

Methylation profiling by the McrBC/RE method shown above is fast, convenient, and relatively inexpensive. However, the method is not suitable for whole-genome methylation profiling, for two reasons. First, if a given sequence has interspersed methylated and unmethylated sites it will be cleaved into small fragments by both McrBC and MSRE and is therefore excluded from the analysis. The presence of such heterogeneously methylated sequences can be inferred from gaps in coverage when that coverage is many-fold, but the actual methylation profile cannot be deduced. Second, less than 70% of all CpG sites reside in a recognition sequence for either MSRE or McrBC, and no TpCpG sites can be analyzed, as there is no MSRE recognition site that contains this sequence, and McrBC cleavage requires a purine 5' of the CpG dinucleotide. No solution to these problems is apparent, and the limitations of the McrBC/RE method mean that new methods will be required for whole-genome methylation profiling.

Figure 2:
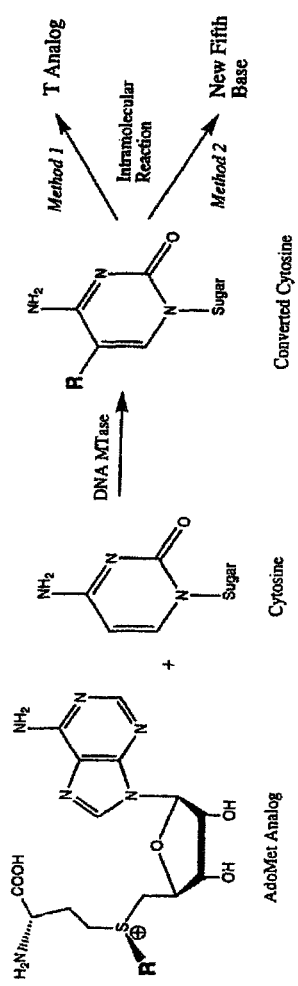
FIG. 2. DNA methyltransferases are able to transfer a wide-variety of functional groups to the 5 positions of cytosines in double stranded DNA with very high sequence specificity. Shown is the transfer of a reactive R group to the 5 position of cytosine that is exploited herein. After incorporation, R can either facilitate oxidative deamination at the 4 position to form a T analog or can directly react with the amino group at the 4 position to make a novel fifth base.
Figure 3:
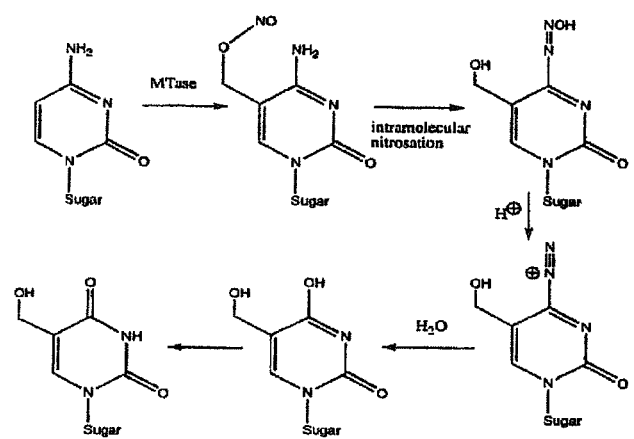
FIG. 3. Example of the transfer of an alkyl nitrite group onto cytosine to facilitate the conversion of cytosine into a thymidine analog. The acid treatment at the third step occurs in buffered solution, pH 3-4, for 3 hrs at 25° C.

Previous studies from the Klimasauskas and Weinhold groups (Dalhoff at al., 2006a, 2006b) have shown that a wide variety of functional groups can be efficiently transferred by DNA methyltransferases to the 5 position of cytosines in DNA by means of synthetic AdoMet analogs in which the methyl group has been replaced by any of a wide variety of functional groups (FIGS. 2 and 3). Bulky groups such as biotin can be added to every recognition site for a given methyltransferase. Here DNA methyltransferase SssI can be used to transfer specific reactive groups to the S position of cytosines in every unmethylated CpG dinucleotide; non-CpG cytosines will not be modified. If the cytosine is methylated, this reaction will be blocked—only unmethylated CpG dinucleotides will be derivatized. The most important aspect of the transferred group is that it alters base pairing during sequencing or during amplification by PCR so as to allow discrimination of CpG dinucleotides that were methylated or unmethylated in the starting DNA. The method is conceptually related to bisulfite genomic sequencing, but does not suffer from the deficiencies that render BGS unusable in whole-genome methylation profiling.

Here are disclosed different methods to distinguish methylated and unmethylated CpG dinucleotides by either converting the cytosine to a thymidine analog or to a new fifth base (neobase X). In the first method, after polymerase extension, the converted cytosine will be replaced by thymidine and the methylation state can be read out as in the case of bisulfite genomic sequencing. In the second method the neobase X must be able to pair specifically with a novel partner Y in similar fashion as A:T or G:C pairs. This new pair must be both stable in double stranded DNA, and must be incorporated by DNA polymerases. X:Y neobase pairs are designed to be stabilized through hydrogen bonding and base stacking interactions, both of which have been shown to be important for the incorporation and selectivity of alternative nucleotides during polymerase extension (Matray and Kool, 1999). The methylation state can then be determined by modifying the sequencing chemistry (either ligation, polymerase, or hybridization based) to sequence with six nucleotides as opposed to the customary four. The rationale is shown in FIG. 2.

Enzyme-Aided Conversion of Unmethylated Cytosines to Thymine Analogues.

Derivatives of AdoMet are synthesized that contain active groups at the sulfonium that SssI transfers to the 5 position of unmethylated CpG dinucleotides so as to convert the target cytosine to an analogue that base pairs as a thymine (FIG. 3).

Figure 4:
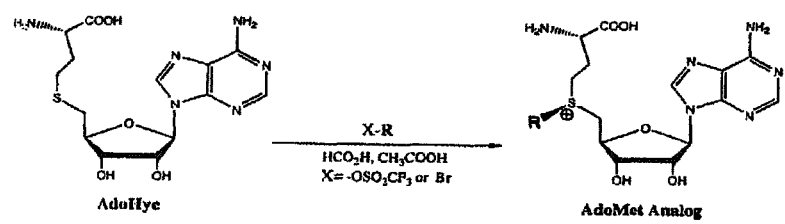
FIG. 4. General scheme for the synthesis of AdoMet derivatives.
Figure 5:
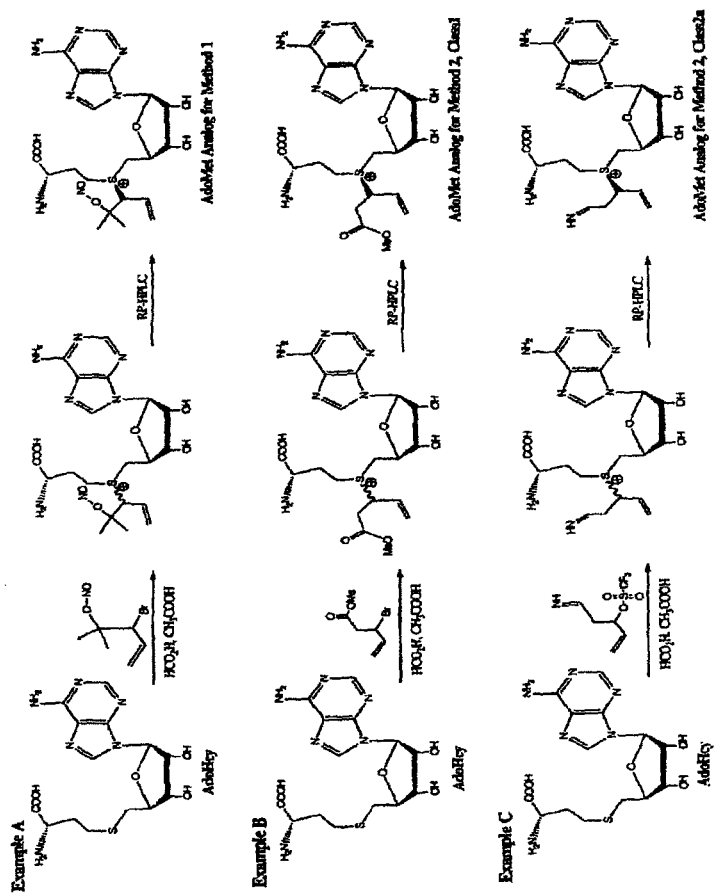
FIG. 5. Examples of the synthetic methods for AdoMet derivatives. Example A shows a scheme for the synthesis of an analog for Method 1. Examples B and C show schemes for the synthesis of analogs for Method 2, Class 1 and 2a analogs respectively. Other analogs for each method will be synthesized in a manner similar to the examples shown. Synthesis of the necessary precursor compounds is shown in FIG. 7.

Specifically, synthesis of AdoMet analogs with the desired extended side chains is performed by regioselective S-alkylation of AdoHcy with corresponding triflates or bromides under mild acidic condition (FIG. 4). For each specific R group containing different functionalities (ester, imine or nitrite), either triflates or bromides will be explored to achieve higher yield for the expected AdoMet analogues. A diasteromeric mixture at sulfonium is expected after alkylation of AdoScy, and further RP-HPLC (reverse phase high performance liquid chromatography) purification will be conducted to isolate the enzymatically active S-epimer for subsequent study. Syntheses of various triflates or bromides can be carried out following reported methods either directly or with slight revision as necessary (Dalhoff et al 2006A,B; Ross et al. 2000). Examples of the synthesis route for several AdoMet analogs are shown in FIG. 5.

In this method, SssI is used to transfer a reactive group to the position of unmethylated cytosines that can facilitate the site-directed oxidative deamination at the 4 position on the cytosine (FIG. 3). This achieves the same results as bisulfite treatment, with an important distinction—the entire reaction is restricted to cytosines in CpG dinucleotides. Full bisulfite conversion affects ~700 million cytosines, while full conversion of unmethylated CpG sites will affect only ~11.2 million. The amount of information retained is therefore almost 70 times greater, and mapping to the genome will be much more efficient.

Figure 6:
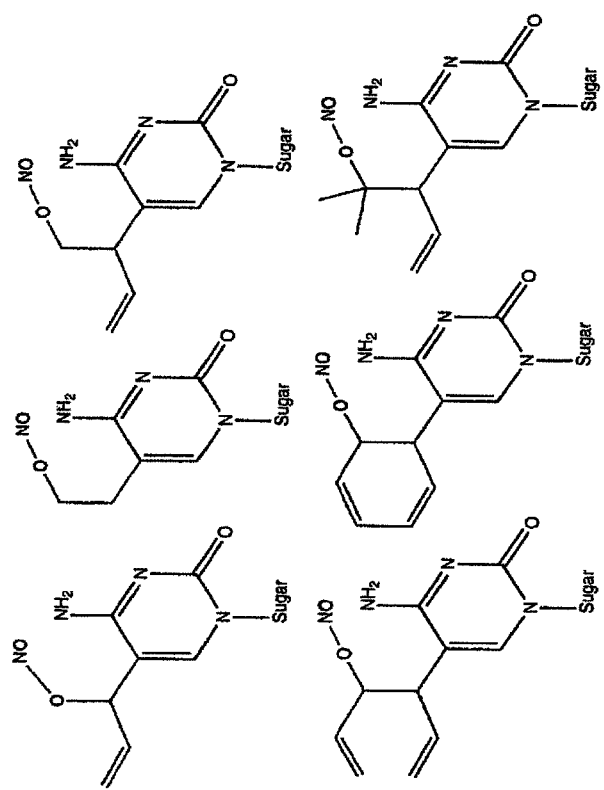
FIG. 6. Library of cytosines modified at the 5 position that will be tested to facilitate the conversion of cytosine into a thymidine analog.
Figure 7:
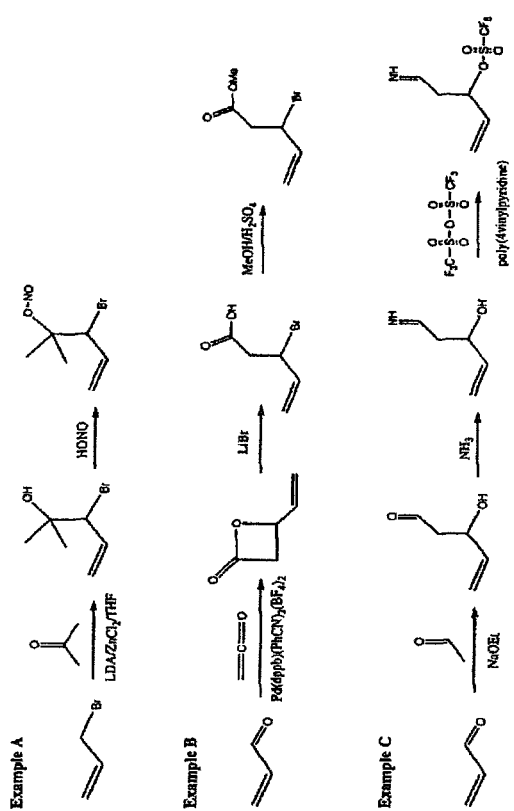
FIG. 7. The synthesis of the precursors for the synthesis of the AdoMet analogs in FIG. 6 are shown.

After the reaction that converts unmethylated cytosines to thymidine analogues, an inert "tail" from the added reactive groups remains at the 5 position of the cytosine. This tail extends into the major groove of the DNA helix, and it is known that modification of this position does not interfere with incorporation of nucleotides during polymerase extension, and this position has been modified in a large number of applications (Ju, et al., 2006). Polymerase-catalyzed labeling of DNA and RNA with bulky adducts such as biotin, digoxigenin, and very large fluorescent moieties involve cytosine analogues that are modified at the 5 position. Such modifications do not strongly interfere with the efficiency or specificity of dNTP incorporation. An initial list of the library of analog Compounds that is tested is shown in FIG. 6 and synthetic routes to the precursors of each of these analogs are shown in FIG. 7.

Short synthetic templates with both methylated and unmethylated CpG and CpH (H=A, C, or T) sites are used to test the incorporation efficiencies of the new compounds. Conversion at each step is assessed by MALDI-TOF MS (matrix assisted laser desorption and ionization time-of-flight mass spectrometry). Longer DNA fragments are treated with HpaII methyltransferase to methylate a subset of CpG sites. After conversion as shown in FIG. 6, replication of the converted template is performed by standard PCR. PCR products are cloned and standard Sanger sequencing is used to determine the levels of conversion. The result is considered positive if HpaII sites remain in the final sequence while all other CpG dinucleotides are converted' to TpG.

The method shown in FIG. 2 gives the same beneficial result as BSG, but without conversion of non-CpG cytosines that makes much sequence data unmappable, without chain breaks, greatly reduced PCR bias, is much more rapid, and does not involve hazardous compounds. After confirmation of efficacy on DNA methylated in vitro by SssI, the method is fully validated by ultrahigh throughput DNA sequencing.

Enzyme-Aided Conversion of Unmethylated Cytosines to a Novel Fifth Base that Specifically Pairs with a Synthetic Sixth Base.

Figure 8:
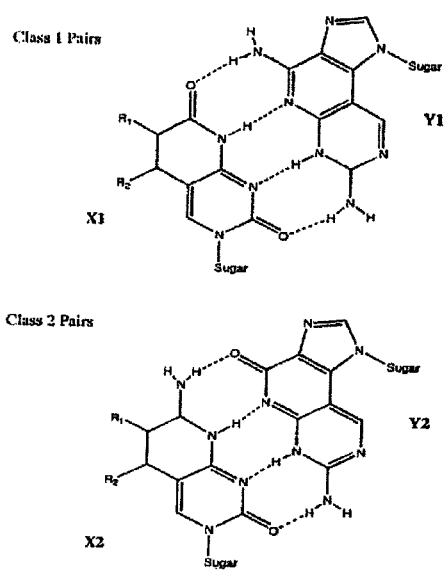
FIG. 8. New classes of neobase pairs (X:Y). Base pairing these can be divided into 2 basic classes of compounds.

In this method, unmethylated cytosines at CpG sites is converted to a new fifth base X (neobase X). Each newly converted neobase X needs to have a partner neobase Y that will form a new base pair in PCR and sequencing reactions. The neobase X:Y pairs are shown in FIG. 8. The neobase Xs are designed such that the group added at the 5 position of the cytosine reacts directly with the amino group at the 4 position of cytosine to form a new six-member ring. Compounds have been broken into two classes based on their hydrogen bonding characteristics after conversion. This reaction introduces a fourth hydrogen bond. Compounds containing two six-member rings for the base have been shown to be incorporated into DNA by polymerase reactions (Henry, at al., 2003). In addition, similar compounds, which form hydrogen bonds at four sites, have been shown to be incorporated into stable duplex DNA (Hikishima, at al., 2005).

The neobases have been designed with C1'-C1' distances similar to the standard Watson-Crick base pairs, which has been shown to be important for enhanced stability in the DNA duplex (Hikishima, at al., 2006). While compounds that have a longer C1'-C1' distance have been constructed and shown to form in double stranded DNA, these base pairs destabilize the helix and it is doubtful that they can be successfully used in polymerase extension reactions. (Liu, at al., 2003; Minakawa, at al., 2003). The chemistry for the reactions to go from modified cytosine to neobase X can be found in section II below. The synthesis of the neobase Y is shown later in this application.

Neobases X and Y are synthesized and tested for function during polymerase extension (see synthetic methods below). Short synthetic templates with both methylated and unmethylated CpG and CpH (H=A, C, or T) sites are used to test the incorporation efficiencies of the new compounds. After conversion of the appropriate sites (see section III below), extension reactions containing the four natural nucleoside triphosphates along with the appropriate neobase Y for the fifth base is performed. MALDI-TOP MS is used to analyze extension products. This technique is ideal since both correctly and incorrectly extended products can be easily analyzed by identification of the correct peaks in MS spectra.

The resolution of MALDI-TOF MS (less than 3 daltons) is especially useful for detecting compounds that can extend with both the new partner neobase Y and the natural nucleotides. From the difference in peak heights, we can estimate the relative efficiency for each incorporation event.

It is possible that the rates of incorporation for these modified bases may be lower than those in natural DNA (Henry and Romesberg, 2003); however, since the PCR steps in both emulsion and bridge PCR used by today's Next-Gen sequencers require the use of short DNA templates (typically 150-300 bases, with maximum allowable lengths of ~800 bases), this should not be problematic. Once, an initial set of pairs which allow for efficient extension in this simple test reaction are selected, a larger DNA fragment is cloned and either treated with HpaII methyltransferase to methylate a subset of CpG sites and used as a PCR template or used directly as a PCR template. PCR with all four natural nucleotides as well as the two neobases is carried out. Gel shift assays are used to verify successful amplification of both the converted and unconverted forms. HpaII endonuclease cleavage can be used to assess successful conversion, as converted sites should be resistant to cleavage. For high-throughput sequencing, triphosphate forms of neobase Y is synthesized by enzymatic phosphorylation of the nucleoside and analysis by Sanger sequencing on an ABI 3730 capillary sequencer.

Each compound is tested with a battery of polymerases including, but not limited to, Taq DNA polymerase, HIV-1 reverse transcriptase variants, Klenow fragment, Thermosequenase variants, and 9° N DNA polymerase variants. Previously both HIV-1 reverse transcriptase variants (Sismour, et al., 2004) and Klenow fragment (Matray and Kool, 1999) have been used for the efficient incorporation of new nucleotide analog pairs.

Synthesis of AdoMet Analogs for Use as SssI Substrates

By altering the functionality of R in the AdoMet analogs, it is possible to convert the 4-amino group directly to a carbonyl group (i.e. convert C to a T analog). For this purpose, the use of an alkyl nitrite is most appropriate. Alkyl nitrites (Crookes and Williams, 1988) contained in R so that the 4-amino group can undergo the well-known oxidative deamination in which a good leaving group, diazonium cation, is generated, and subsequent nucleophilic attack at C4 forms the 4-position carbonyl group (FIG. 4). It has been shown that a double bond introduced adjacent to the activated carbon of the SssI substrate facilitates the SssI mediated 5 position addition by the allylic conjugative stabilization of the p orbital at the reactive carbon in the transition state (Dalhoff, at al., 2006a). Taking the electron effects into consideration, the branched alkyl favors the nitrosation of the amino group and an allylic system is also introduced in the R part of the AdoMet analog to facilitate transfer by SssI. A partial list of AdoMet analogs, which are synthesized and studied for their feasibility for SssI-mediated C→T conversion, is shown in FIG. 6.

A library of AdoMet analogs is designed, produced and screened to optimize the suitable SssI substrates as described above. This library is designed such that the activated methylene group in R is efficiently added to the 5 position of cytosine while promoting conversion of C to a fifth base via intramolecular chemical reactions between the introduced functionality and the 4-amino group of cytosine. To this end, the R groups in the AdoMet analogs are expected to be DNA compatible and amino group reactive, and are designed to bear a variety of functionalities including imines, esters, or alkyl chlorides from which corresponding aminals and amides will be readily generated via nucleophilic attack from the 4-amino group. This reaction results in formation of a new ring that contains an extra hydrogen donor or acceptor in addition to the one cytosine provides, while changing the nature of the hydrogen bonding capability at the 4-amino group from hydrogen bond donor to acceptor.

Figure 9:
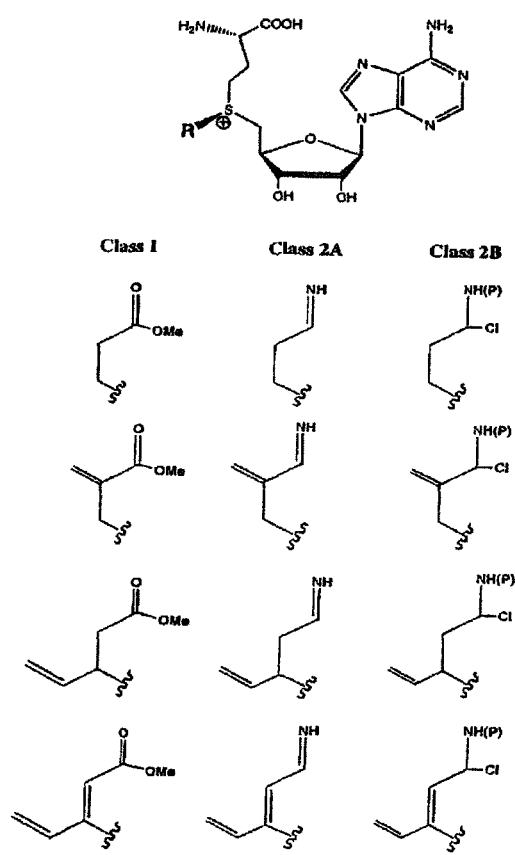
FIG. 9. Library of AdoMet analogs that will be produced to modify the 5 position of cytosine using SssI to produce neobase X.

FIG. 9 shows the library of AdoMet analogs that are synthesized following published methods (Daihoff, et al., 2006b). As above, each of these compounds is designed with a double bond adjacent to the activated carbon of the SssI substrate to facilitate the SssI-mediated addition to 5 position of unmethylated cytosine. All synthetic AdoMet analogs are purified and fully characterized by NMR and high resolution mass spectrometry before use.

Figure 10:
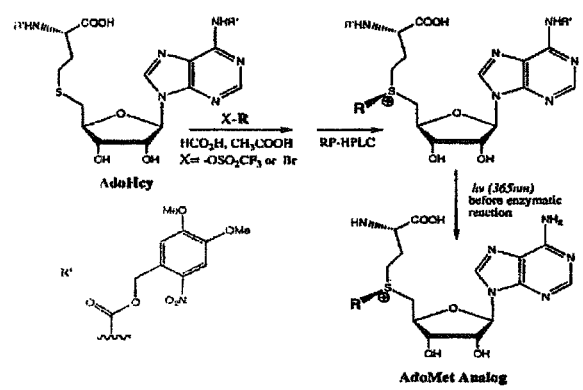
FIG. 10. Example of a method to prepare AdoMet analogs by blocking the amino groups of the AdoMet analog with a photocleavable blocking group. This group will be added to the AdoHyc starting material and the AdoMet analog will be synthesized as described in part II. The reaction to transfer R to the 5 position of CpG sites in the DNA will be prepared and then irradiated with UV light to trigger the removal of the blocking groups and use of the AdoMet analog as a substrate for the enzymatic transfer reaction.

By controlling the synthesis and enzymatic transfer reaction conditions, it is possible to prevent the amino-reactive functionalities contained in the extended chain of the AdoMet analogs from interacting with amino groups in both homocysteine and adenine moieties during the synthesis and transfer processes. Should this occur however the synthetic yield for the above mentioned AdoMet analogs may be compromised. In this event, amino-protected AdoHCy can be used as a starting material instead of normal AdoHcy to synthesize the AdoMet analogs. After synthesis of the amino protected analog, the protective group is removed immediately prior to enzymatic reaction under biologically compatible conditions. This is achieved by using a photocleavable protective group to protect the amino groups. Photocleavable groups have been shown to be ideal reagents for temporary blocking groups in enzymatic reactions since the reaction only needs to be irradiated and no additional reaction components need be added (Seo et al. 2005). An example of one such protective group that can be used in this study is shown in FIG. 10. The shown 6-nitroveratryloxycarbonyl group (NVOC) has previously been Used as an exocyclic amino protective group in nucleotides (Alvarez et al. 1999) and can be easily removed upon irradiation at 365 nm. When the now-protected AdoMet analog is ready for use, the enzymatic transfer reaction can be assembled and irradiated with 365 nm light, which will not damage DNA. Irradiation will trigger the removal of the blocking groups and allow the now unblocked nucleotides to quickly and efficiently be used in the enzymatic alkylation of the 5-position in cytosine, limiting the ability of the AdoMet analogs to interact intramolecularly.

Transformation of Converted Cytosine to Fifth Base

Figure 11:
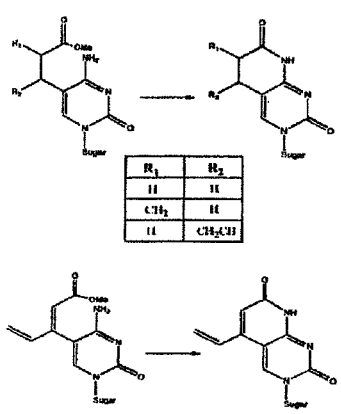
FIG. 11. Alternative methods for the transformation of converted cytosines to Class 1 fifth bases by amide formation.
Figure 12:
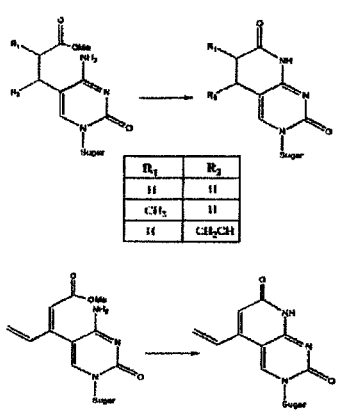
FIG. 12. Alternative methods for the transformation of converted cytosines to Class 2 fifth bases can be achieved through two routes (A and B). The required starting transfer groups are listed as 2A and 2B in FIG. 9.

After addition of the appropriate modification to the 5 position of cytosine using the AdoMet analogs of Method 2, each modified cytosine is converted into a fifth base of the form found in FIG. 8. Schemes showing the conversion of the modified cytosine for each case are shown in FIGS. 11 and 12. Each of these reactions should proceed spontaneously after the addition of the R group. Slight modification of the pH may be necessary in each reaction to increase reaction efficiency.

To directly test the conversion chemistry and it affect on DNA templates, several short synthetic templates are synthesized with both methylated and unmethylated CPS and CpH (H=A, C. T) sites along with their complementary strands. Each template is annealed to its complementary strand to form dsDNA, which is used as a substrate of the SssI reaction with each AdoMet analogue. After transfer of R, products are analyzed by MALDI-TOF MS to determine the efficiency of the transfer reaction. The product is then treated as shown in FIGS. 11 and 12 to convert the modified cytosines. Products are again analyzed by MALDI-TOF to test for conversion. DNA is analyzed by gel electrophoresis to detect DNA breakage, and reaction conditions are modified to eliminate any unexpected breakage that occurs under the mild reaction conditions employed.

Synthesis of New Partners for Converted Cytosines

Since these compounds are initially used in polymerase extension reactions, only the triphosphate forms of Y1 and Y2 are presented (see FIG. 8). Phosphoramidite forms (which allow direct incorporation of the partner via a standard solid phase DNA synthesizer), can be synthesized with slight modifications of the following procedures as appropriate.

Figure 13:
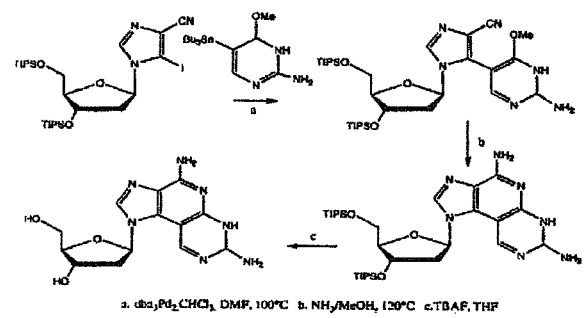
FIG. 13. Synthesis of pairing partner Y1 for Class 1 fifth bases.
Figure 14:
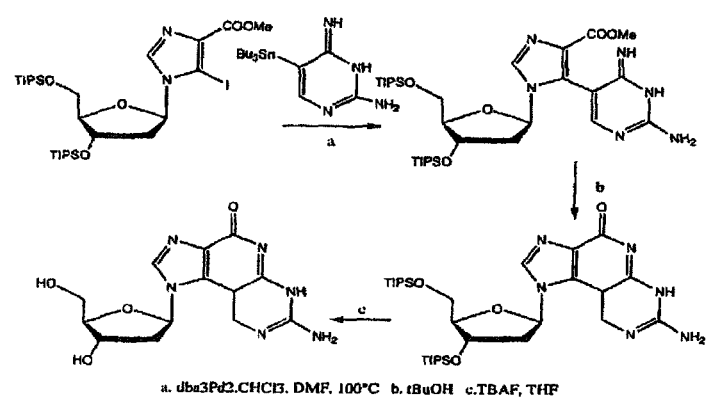
FIG. 14. Synthesis of pairing partner Y2 for Class 2 fifth bases.
Figure 15:
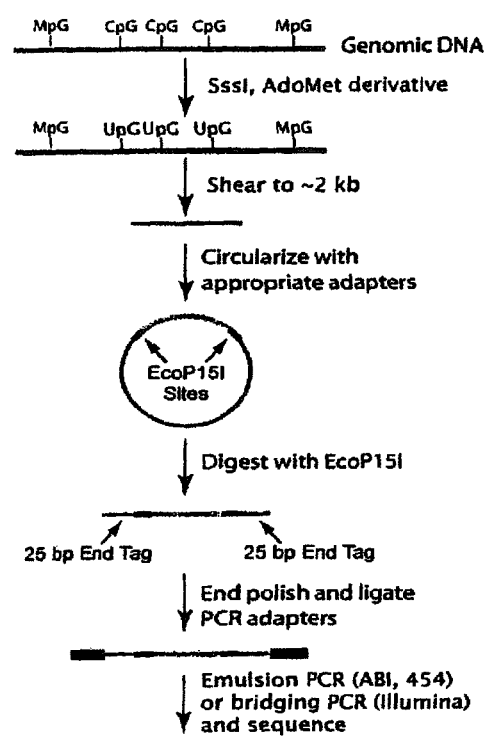
FIG. 15. Pipeline for methylation profiling. Modified cytosines are shown as uridines (U), although they have an additional inert substitution at the 5 position. The ditag library shown can be used directly in ABI SOLiD or 454 sequencing.

Synthesis of partners Y1 and Y2 is performed according to the schemes in FIGS. 13 and 14. Synthesis of the Y1 and Y2 skeleton is performed using a Stille coupling reaction of a 5-iodoimidazole nucleoside with the appropriate tributylstannyl pyrimidine analogs. The desired nucleoside can then be obtained through intramolecular cyclization of 5-pyromidinylimidazole nucleosides (Ohno, et al., 1986). The 5-iodoimidazole nucleoside, synthesized from 2' deoxyinosine, and the tributylstannyl pyrimidine derivatives are synthesized following established procedures (Minakawa, et al., 2003; Minakawa, et al., 1996; De Napoli, et al., 1997).

Ultrahigh Throughput DNA Sequencing of Derivatized DNA

After validation of the chemistry on plasmid substrates methylated at known positions, the methylation patterns are determined of the mammary carcinoma cell line MCF, for which this laboratory has very large amounts of methylation data (see FIG. 1). DNA is purified by proteinase K digestion, phenol extraction, and dialysis against 10 mM Tris HCl, pH 7.2. DNA is than be reacted with the optimal AdoMet derivative identified in Aim 1 or 2 and with SssI (commercially available from New England Biolabs, Inc.). The derivatized DNA is then be subjected to ultrahigh throughput DNA sequencing, and CpG dinucleotides in the NCBI reference sequence that appear at TpG or CpA are judged to have been unmethylated CpG dinucleotides in the starting DNA.

Astounding advances in DNA sequencing technology have increased throughput enormously. The ABI SOLiD (sequencing by oligo ligation and detection) have produced single sequence runs of >9 gigabases at a reagent cost of ~$7,600 per run. 3× coverage per run is now possible, and ongoing improvements in the technology will increase throughput and reduce cost per run throughout the course of the proposed research.

The nature of ultrahigh throughput DNA sequencing increases the robustness of the sequencing chemistry. Recall that SOLiD, Illumine, and 454 all start from single DNA molecules that are amplified on a solid support (beads in the case of SOLiD and 454, and a glass surface in the case of Illumina). If incorporation of adenine or neobase Y is not 100% efficient at the amplification step, a mixed signal (adenine plus guanine or neobase Y and guanine, as appropriate) will be recorded during sequencing. As all DNA molecules are clones of a single starting DNA molecule, a mixed signal indicates that the CpG site in questions was unmethylated in the starting DNA. Full information as to methylation status can be achieved even if replacement of the guanine opposite the derivatized cytosine is not 100% efficient.

EXPERIMENTAL RESULTS REGARDING IMPORTANCE OF METHYLATION

The human genome contains ~28 million CpG sites, about 60% of which are methylated at the 5 position of the cytosine. Methylation of relatively CpG-rich promoters causes strong transcriptional repression (Stein R, Razin A, Cedar H. (1982); Lorincz M C, Schübeler D, Hutchinson S R, Dickerson D R, Groudine M. (2002)) and many experiments have demonstrated faithful inheritance of methylation patterns over many cell divisions in mammalian somatic cells (Lorincz M C, Schübeler D, Hutchinson S R, Dickerson D R, Groudine M. (2002); Wigler M, Levy, D, Perucho M. (1981)). This heritability means that genomic methylation patterns could have many biological functions, and many such functions have been proposed over the past 50 years. However, much controversy as to the biological roles of genomic methylation patterns remains because of the lack of information about the genome-wide structure of methylation patterns. A further concern is the common use of cultured cells in methylation profiling studies; genomic methylation patterns are unstable in cultured cells, and promoters of tissue-specific genes that are methylated in cultured cells are usually unmethylated in both expressing and non-expressing tissues (Jones P A, Wolkowicz M J, Rideout W M 3rd, Gonzales F A, Marziasz C M, at al. (1990)).

Half of all CpG sites are contained in repetitive DNA (Rollins R A, Haghighi F, Edwards J R, Das R, Zhang at al (2806)), but existing methods of methylation profiling are largely or completely unable to evaluate methylation at dispersed and tandem repeated sequences. This is a severe shortcoming, as the methylation of such sequences can have strong effects on phenotype. Human ICF (immunodeficiency, centromere instability, and facial anomalies; OMIM 242860) syndrome is caused by mutations in the DNMT3B gene that prevent methylation of specific classes of tandem repeated sequences (Xu G. L, Bestor, T H, Bourc'his D., Hsieh C-L, Tommerup, N, et al. (1999)), while Fragile X mental retardation syndrome (OMIM 300624) is caused by de novo methylation provoked by expansion of a (CGG) repeat tract at the FMR1 locus (Sutcliffe J S, Nelson D L, Zhang, F, Pieretti, M, Caskey C T et al. (1992)). Transposon insertion alleles of mouse genes such as Agouti and Axin show highly variable penetrance and expressivity that are dependent on the methylation state of the transposon (Michaud, E. J., van Vugt, Hultman, S. J., Sweet, H. O., Davisson, M. T. (1994); Rakyan V K, Preis J, Morgan H D, Whitelaw, E. (2001)

Here, a method called Methyl-MAPS (methylation mapping analysis by paired-end sequencing) is disclosed that can provide coverage of up to 82.3% of the CpG sites in the genome. This method probes methylation status at single copy and repetitive elements, each of which represents ~50% of the CpGs in the genome (Rollins R A, Haghighi F, Edwards JR, Das R, Mang et al (2006)). The method combines enzymatic fractionation of the genome into methylated and unmethylated compartments with deep sequencing to provide a comprehensive profile of genomic methylation patterns. A comparison of Methyl-MAPS to other techniques for methylation profiling shows that Methyl-MAPS provides high coverage of single copy and repeated sequences at relatively low cost. Methyl-MAPS is applied herein to determine the structure of genomic methylation patterns at both fine and gross levels and have found sequence contexts and specific chromatin marks that are tightly associated with methylation status. The method disclosed hereinabove employing conversion of unmethylated cytosines to thymine analogues is expected to give superior results.

The methylated compartment of the genome was isolated by digestion with five methylation-sensitive restriction endonucleases (RE), while the unmethylated compartment was isolated by limit digest with the methylation-dependent McrBC complex. Paired-end libraries were prepared, and 25 bases from both ends of each DNA molecule were determined by sequencing-by-ligation on AB SOLiD™ DNA sequencers. CpG methylation was then determined by analyzing which CpGs were resistant or sensitive to cleavage by McrBC or RE. The use of paired-end sequencing allows direct determination of the methylation status of interspersed repeated sequences, as in the majority of cases one or both end tags are anchored in unique sequence. A total of 16,180, 663 unmethylated sequences and 20,218,244 methylated sequences from somatic DNA were mapped to unique locations in the genome (hg18, mm9), and mean coverage was 13.1×. The methylation status of 152,693,954 CpG dinucleotides was determined in human breast DNA, 70,294,069 in human brain DNA, and 52,819,963 in mouse brain DNA for a total of 275,807,986 CpG sites.

Validation of the Methyl-MAPS approach was done by comparison to bisulfite methylation analy-sis on the Illumine Infinium HumanMethylation 27 beadchip. The Pearson's correlation coefficient for methylation data obtained via the two unrelated methods was 0.84 for breast 1 and 0.87 for breast 2. This is substantially greater than correlations obtained by pair wise comparison of other DNA methylation profiling methods (Irizarry R A, Ladd-Acosta C, Carvalho B, Wu H, Brandenburg S A, (2008)). To further confirm that accurate methylation data were obtained by Methyl-MAPS, sequences known to be methylated on the female X chromosome and at imprinted loci were examined. Promoter-associated islands on female ChrX were much more methylated than were promoter-associated islands on the male ChrX, whereas islands on male and female autosomes were less methylated. An analysis of all known differentially methylated regions (DMRs) at imprinted loci showed DMRs to be methylated at intermediate densities, as expected for sequences subject to allele-specific methylation.

Figure 16:
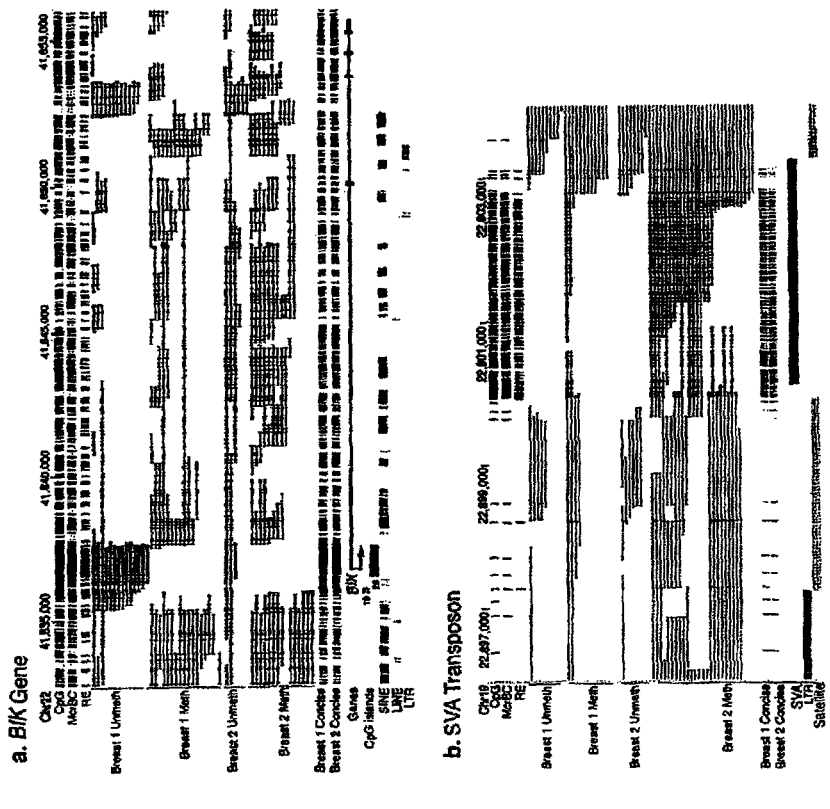
FIG. 16. High-resolution genome wide methylation profiling and genome-wide DNA methylation trends. (a) UCSC browser view of Methyl-MAPS data from the genomic region spanning the BIK gene. Individual mapped sequence reads are shown in the upper raw data tracks. Dark gray sequences were resistant to methylation-sensitive restriction endonucleases (RE) and are therefore methylated. Darkest gray sequences were resistant to the methylation-dependent McrBC complex and are unmethylated. Tick marks both in tracks along the top of the figure and within each sequence indicate locations of individual RE and McrBC recognition sequences, respectively. Methylation data is also presented in a concise view, where each CpG is assigned a methylation score from the ratio of methylated to total (unmethylated and methylated) sequences covering each CpG site. The bulk of the BIK gene is methylated while the CpG-rich promoter and first exon are unmethylated. (b) Methylation of the SVA retrotransposon in a repeat-rich region of Chr19. While the CpG density is comparable to that of the CpG island of the BIK gene shown in a, the SVA retrotransposon is densely methylated.

The methylation status of the BIH (BCL2 interactor and killer) gene in DNA from normal human breast tissue is shown in FIG. 16a. The pattern of methylation of this gene is typical in that the CpG-rich promoter and first exon are unmethylated, whereas the bulk of the gene is methylated. Methyl-MAPS can be used to directly measure the methylation of repetitive sequences, as shown in FIG. 16b. The SVA retrotransposon in this repeat-rich genomic region is densely covered by methylated fragments, which is typical of both dispersed and repeated sequences in the mam-malian genome.

Figure 17:
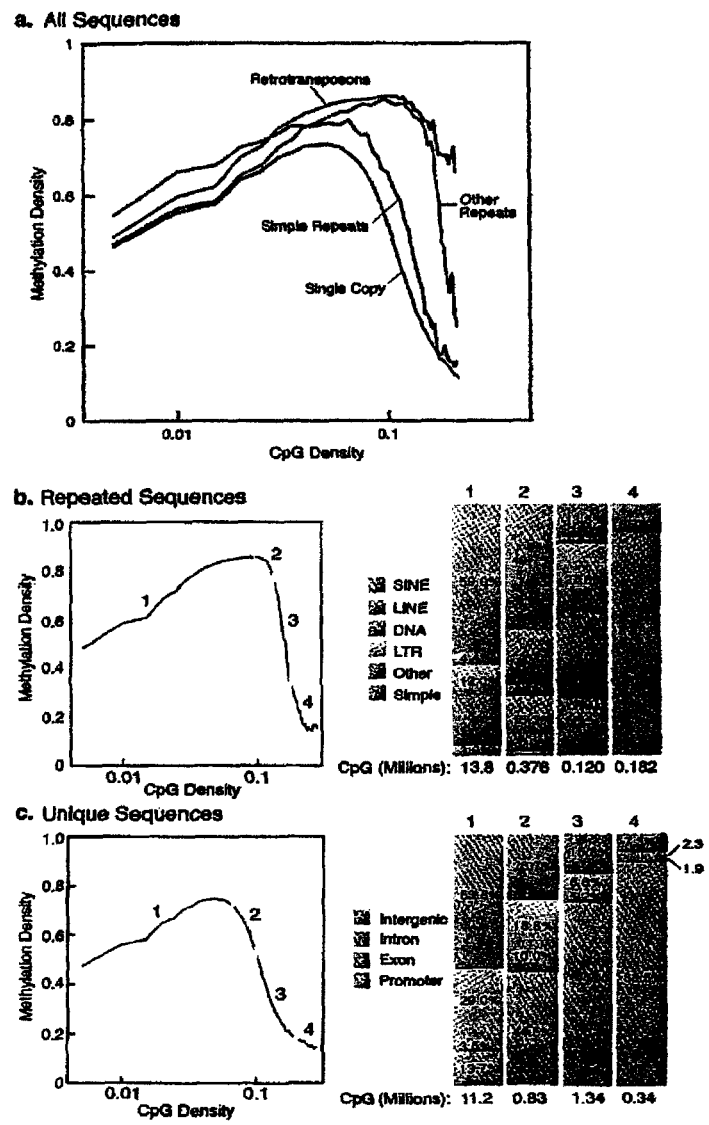
FIG. 17. Relationship of CpG and methylation density for repeated and unique sequences. (a) CpG methylation is plotted as a function of CpG density for four distinct genomic compartments (single copy, retrotransposons, simple repeats and other repeats). Approximately 50% of the CpGs in the genome are contained in both repeats (b) and unique sequences (c). Each curve is divided into four CpG density regions, the CpG composition of each is shown in the bar charts on the right. The large majority of CpGs are contained in region 1 in both plots (A, 96%; B, 81.9%) (b) The majority of low-CpG density CpGs are contained in SINE and LINE elements, while the highly unmethylated high density CpGs are primarily found in simple repeats. (c) The majority of low-CpG density CpGs are contained in intergenic and intronic unique sequences, while the highly unmethylated high density CpGs are primarily found in promoter-associated regions.

Analysis of the observed methylation patterns revealed a significant relationship between CpG density and methylation density (FIG. 17). Previously, it has been established that regions of high CpG density in promoters are largely unmethylated 11; however, only promoter regions were studied and the relationship between CpG density and methylation at non-promoter sequences and in repeats has not been elucidated. In single copy DNA, the fraction of methylated CpGs was found to increase with CpG density up to a density of 0.025 (one out of 40 nucleotides is a C in a CpG dinucleotide), where 60% of the CpG sequences were methylated (FIG. 17a,c). This trend is followed by over 90% of the CpGs found in single copy sequence. At higher CpG densities, methylation density fell off sharply, and methylation of unique sequences was lowest at very CpG-rich promoters. A similar pattern was seen for repeated sequences (FIG. 17b); for these sequences, methylation increased up to a CpG density of 0.07 (one out of ~15 nucleotides is a C in a CpG dinucleotide) where 80% of CpGs were methylated; thus these repeated sequences, which are largely composed of transposable elements, continue to be methylated at very high CpG densities. Methylation in repeated sequences was low only in CpG-containing simple sequence repeats of 2-6 nucleotides. These methylation patterns were very similar in human breast and brain DNA, and in mouse brain DNA, and indicate that these trends are fundamental features of the methylation program in mammalian somatic tissues. The unmethylated, CpG-dense compartment was found to be populated by two very different sequence types; single-copy promoter-associated CpG islands (FIG. 17c) and simple sequence repeats of 2 to 6 nucleotides (FIG. 17b).

Figure 18:
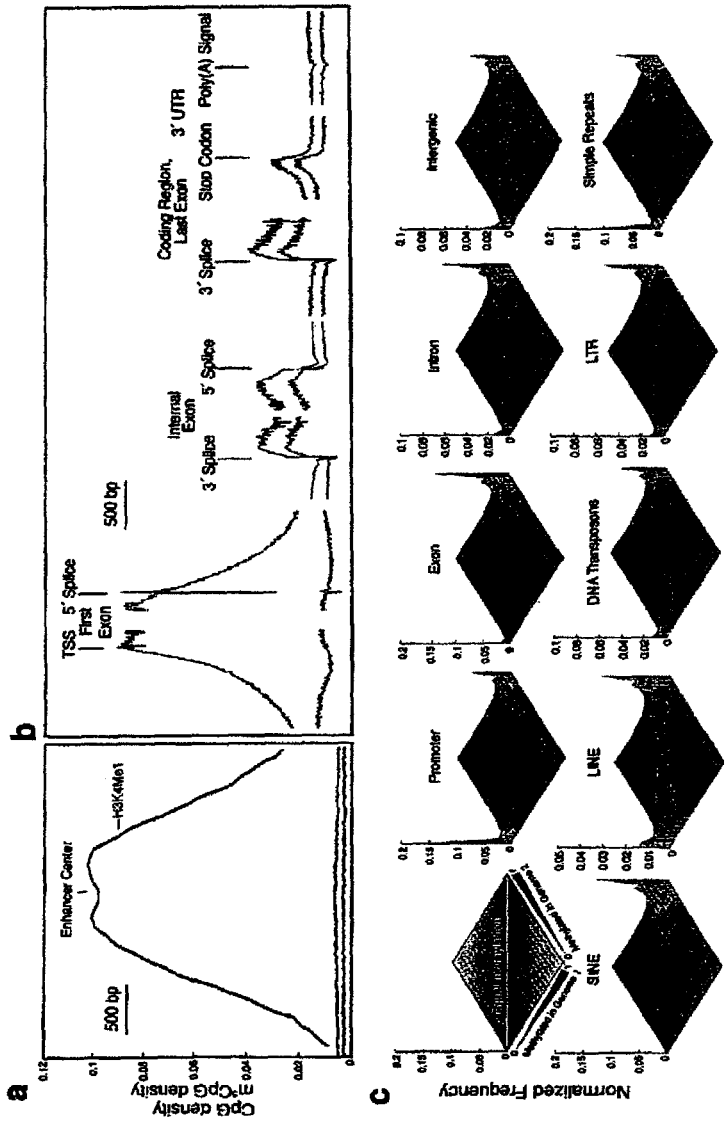
FIG. 18. (a) CpG distributions and methylation patterns in 16,181 human genes. m5CpG and CpG densities are shown in relation to TSS, exon splice sites, stop codons, and poly(A) sites. Note spikes in CpG and m5CpG densities at the 5' and 3' ends of exons and internal to the stop codon in the last exon. (b) Comparison of methylation patterns in normal breast tissue from two individuals. Methylation status of each CpG with high coverage (>6x) is computed for each sample. The frequency of such points is then plotted as a function of the methylation score for each sample. Heat map indicates frequency (light gray="hot"; dark gray="cold"). Values in the left corner are unmethylated in both samples. Values in the right corner are methylated in both samples. Values along the horizontal equivalently methylated in each sample. Some sequence classes have a wide-range of methylation states, such as intronic and intergenic single copy sequences and LINEs, LTRs and DNA transposons. Other classes such as SINEs, exons, simple repeats and promoters are polarized. (c)

FIG. 18 shows DNA methylation and CpG distributions averaged across 16,181 RefSeq genes. As expected from the existence of CpG islands at most promoters, the density of CpG dinucleotides was very high in first exons, with the high CpG density extending well 5' and 3' of the first exon. These cpGs were under methylated, with the density of unmethylated CpGs reaching a maximum at the transcription start site (TSS). CpG-poor promoter regions are partially methylated, but the methylation density is likely to be too low to enforce transcriptional silencing (Weber M, Hellmann I, Stadler M B, Ramos L., Pääbo S., (2008); Kass S U, Landsberger N, Wolffe A P (1997)). FIG. 18c shows that methylation status across multiple sequence compartments is very similar between unrelated individuals.

The data in FIG. 17b indicate that CpG islands near transcriptional start sites (TSS) are unmethylated; however, only ~40% of computationally annotated CpG islands are located near TSSs. Analysis of length and methylation density showed that non-TSS islands were much more likely to be methylated and were much shorter than were TSS islands. Both tendencies were less pronounced for intergenic CpG islands, some of which may be associated with novel TSSs for genes that encode unknown transcripts.

Within coding regions of genes, unanticipated patterns of methylation were found at the borders of exons. An increase in the density of CpG sites was observed at the 5' and 3' ends of internal exons (Majewski J, Ott J (2002)), and these CpG sites were relatively highly methylated. As can be seen in FIG. 18b, the sequence compartments in which the fraction of unmethylated CpG sites is lowest are SINE (largely Alu) transposons and internal exons of cellular genes. The presence of densely methylated coding exons was surprising, as 5-methylcytosine (m5C) is a premutagenic modified base that leads to C→T mutations at a rate 18-fold higher than the average of all other point mutations (Kondrashov A S (2003)). The high methylation and CpG densities at exon ends could increase the efficiency of splice site selection via recruitment of MeCP2, which has been reported to bind to m5C and has been reported to be required for accurate pre-mRNA splicing (Young J I, Hong E P, Castle J C, Crespo-Barreto J, Bowman A B at al. (2005)); however, the increase in CpG density and methylation density is also apparent just 5' of the stop codon, which is not associated with a splice site.

Figure 19:
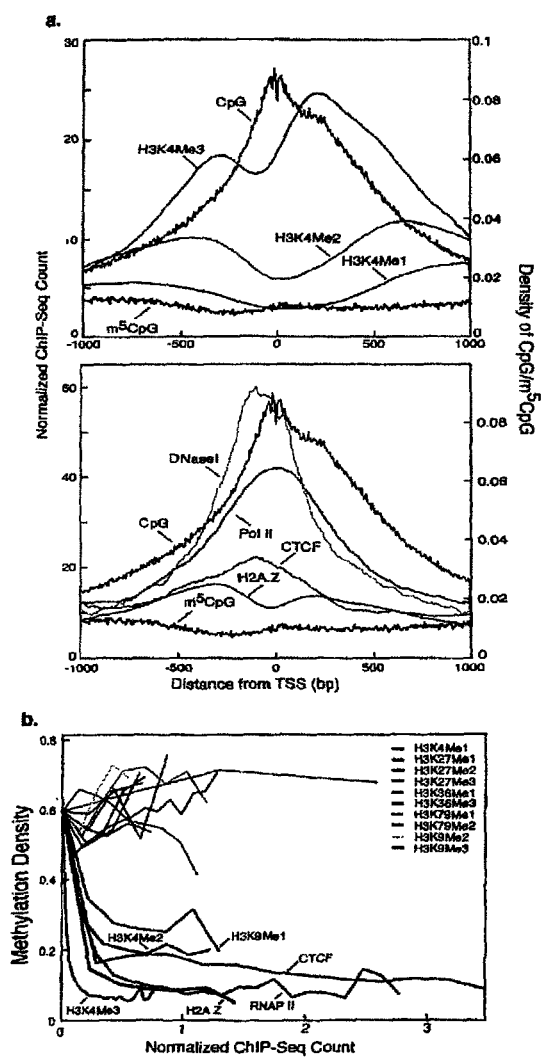
FIG. 19. Relationship between DNA methylation, histone modification, chromatin proteins and nucleosome positioning. (a) m5CpG and CpG densities, ChIP-Seq scores, and DNase hypersensitivity scores are plotted relative to promoter TSSs for 16,181 RefSeq genes. (b) CpG methylation plotted as a function of histone modifications, chromatin factors, and RNA polymerase II occupancy. Note the strong negative relationship between DNA methylation and density of H3K4me3 and H2A.Z and the lack of a strong association between DNA methylation status and most histone modifications.

There is considerable interest in the relationship between DNA methylation and histone modifications. Large databases that describe the distribution of histone modifications and chromatin proteins over the genome have been derived by chromatin inmunoprecipitation (Barski A, Cuddapah S, Cul K, Rob T Y, Schones D E, at al. (2007); Mikkelsen T. S. Ku M, Jaffe D B, Issac B. Lie-berman E, at al. (2007)) or DNaseI cleavage (Boyle A P, Davis S, Shulha H P, Meltzer P. Margulies E H, et al. (2008)) followed by deep sequencing. These data were used to test for correlations of histone variants and bound chromatin proteins with patterns of DNA methylation. H3K36 methylation, H3K27 methylation, H3K79 methylation, H3K9 di- and tri-methylation showed no strong correlation with DNA methylation (FIG. 19). In contrast, di- and trimethylation of lysine 4 of histone H3 (H3K4) showed a strong negative correlation with DNA methylation. While previously it was shown that H3K4Me2 was associated with unmethylated promoters (Weber M, Hellmann I, Stadler M B, Ramos L., Pääbo S., (2008)), it is interesting that little correlation was found with H3K4Me1 and the strength of the correlation increased with the level of modification at H3K4. This is consistent with the finding that de novo methylation is targeted to DNA sequences associated with histones that are unmethylated at H3K4 via a domain in the methylation regulator DNMT3L that specifically recognizes unmethylated H3K4 (Ooi S K. Qiu C, Bernstein E, Li K, Jia D, et al. (2007)).

The binding of the H2A.Z histone variant correlates inversely with DNA methylation (FIG. 19), demonstrating that these two marks may be mutually exclusive in mammals, as was found recently in plants (Zilberman D, Coleman-Derr D, Ballinger T, Henikoff S. (2008)). Binding of CTCF also correlated globally with unmethylated DNA, in agreement with previous reports that CTCF binds to unmethylated DMRs at specific loci (Bell A C, Felsenfeld G. (2000); Hark, A. T. Schoenherr C J, Katz D J, Ingram R S, Levorse J M at al. (2000)). DNA methylation patterns have been shown to be subject to somatic inheritance in mammals, whereas there is little evidence for the mitotic inheritance of histone marks and histone variants. Analysis of CpG loss rates indicates that the genomic methylation patterns observed in somatic cells are similar to those of male germ cells.

Figure 20:
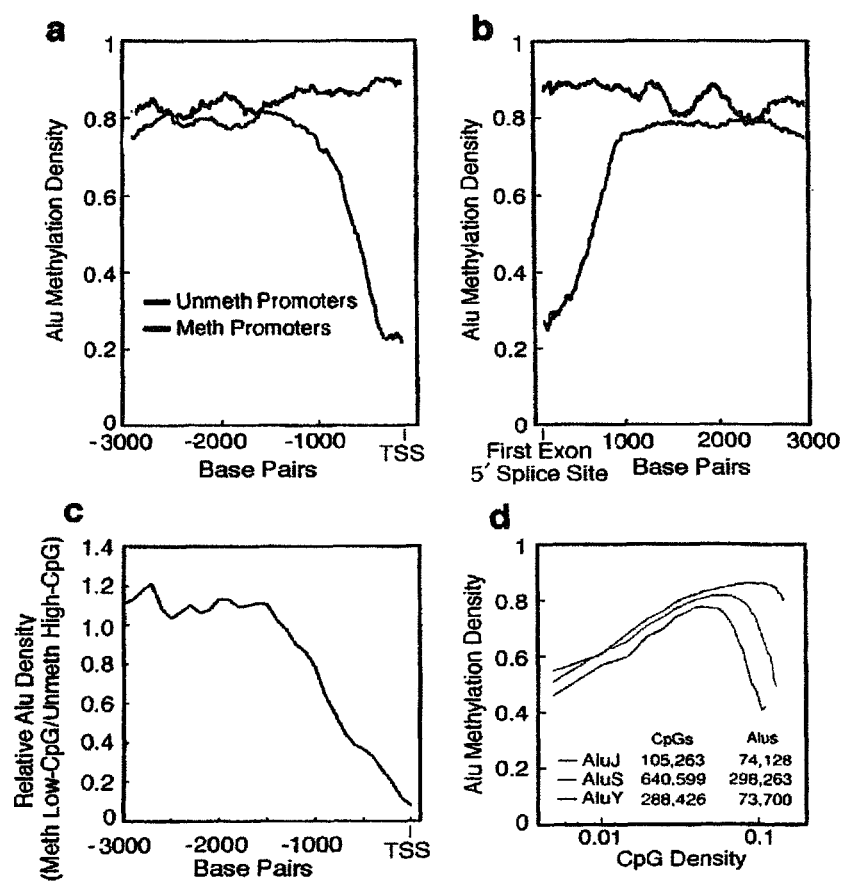
FIG. 20. Relationship between CpG methylation at Alu retrotransposons and proximity to methylated and unmethylated promoters. Alu methylation is plotted as a function of distance from the TSS (a) and to the 3' splice site of the first exon (b) of methylated (gray) and unmethylated (black) first exons. When near unmethylated first exons Alu elements are also unmethylated. Alu methylation correlates with first exon methylation when Alus are within ~1 kb of the TSS or 3' edge of the first exon. (c) Negative selection of Alu elements near unmethylated promoters correlates. The ratio of the fraction of methylated promoters with Alus near the first exon to the fraction of unmethylated promoters with Alus near the first exon is plotted as a function of the distance to the TSS. This suggests that unmethylated Alus near promoters are deleterious and are lost from the population by selection. (d) The methylation status of the three major classes of Alu retrotransposons. Note that AluY (the only active Alu in the human genome) remains heavily methylated at higher CpG densities.

The data of FIGS. 17 and 18 suggest that the domains around CpG-dense promoters may be inherently refractory to DNA methylation. To test this hypothesis the methylation status of Alu elements that are located near promoters was examined. Alu elements are normally highly methylated (FIG. 20d), but Alu elements located within ~1000 base pairs of unmethylated first exons tend to be unmethylated (FIG. 20a,b). This supports the hypothesis that single-copy CpG-rich regions are shielded from the DNA methylation machinery. Interestingly, Alu elements are also depleted from these unmethylated domains, which suggests that Alu elements that insert into these unmethylated regions reduce host fitness and are lost from the population by selection.

DNA methylation has long been believed to regulate gene expression via programmed removal of DNA methylation from promoters by passive or active methylation to allow lineage-specific gene expression. Arguments against this model have been raised (Walsh C P, Restor T H. (1999)) and it has recently been reported that the gain of DNA methylation at promoters in cells differentiating in vitro is much more prevalent than is a loss of promoter methylation (Heintzman N D, Hon G C, Hawkins R D, Kheradpour P, Stark A, et al. (2009)). It has recently been shown that the patterns of histone modification and histone variants at promoters are only weakly related to the level of expression of genes, while chromatin modifications at enhancers are strongly associated with cell type-specific gene expression (Mohn F, Weber M, Rebhan M, Roloff T C, Richter et al. (2008)). We examined the CpG and methylation density of 27,065 enhancers identified by Heintzmann et al. and found that enhancers are characterized by very low levels of CpG and DNA methylation (FIG. 18a). This indicates that enhancer methylation is unlikely to be involved in cell-type specific gene expression. The lack of cell type-specific methylation at either enhancers or promoters indicates that DNA methylation is likely to have a negligible or very small role in development, and that the methylation changes seen at some low-CpG promoters are likely to be a result of transcriptional activation rather than a cause.

Our genome-wide data reveals features of methylation patterns that were not apparent in pre-vious experiments that covered small fractions of the genome (Weber M. Hellmann I, Stadler M E, Ramos L., Pääbo S., (2008); Meissner, A. Mikkelsen T S, Gu H, Wernig M, Hanna J, et al. (2008); Eckhardt, F. Lewin J, Cortese R. Rakyan V K, Attwood J, et al. (2006)) or have known biases with respect to CpG density (Down T A Rakyan V K, Turner D J, Flicek P, Li H, et al. (2008)). The likelihood of methylation of a CpG dinucleotide depends in part on the local sequence environment: high CpG density increases the probability that a CpG will be methylated up to a limit, after which very high CpG densities repel DNA methylation. This trend includes exonic CpGs, which tend to be methylated. Other factors that have been implicated in shaping genomic methylation patterns include the piRNA pathway, which targets classes of transposons for de novo methylation specifically in male germ cells (Lin I G, Tommynski T J, Cu Q, Hsieh, C L. (2000)), and the binding of transcription factors, such as Sp1 to methylated target sites, which can induce demethylation of local CpG sites in dividing mammalian cells (Carmell M A, Girard A, van de Kant N J, Bourc'his D, Bestor T H, et al. (2007); Matsuo K Silks J, Georgiev O, Marti P, Giovannini N, at al. (1998)).

Collectively these data suggest that methylation is the default state of nucleosomal DNA and could explain how genomic methylation patterns are established and maintained by DNA methyl-transferases whose sequence specificity is limited to the CpG dinucleotide. The heritability of genomic methylation patterns clearly shows that once established DNA methylation is dominant over chromatin modifications. Sequences such as imprinting control regions, CpG islands of the inactive X chromosome, and some transposons and retroviruses are methylated as a result of poorly-understood pathways that direct de novo methylation specifically to these sequences. The data indicate that the bulk of the genome is methylated as the default state, and unmethylated regions are protected from a promiscuous DNA methylating system by a combination of very high CpG densities and histone modifications and variants (di- and trimethylated H3K4 and H2A.Z) that repel DNA methyltransferase complexes.

In conclusion, abnormalities of genomic methylation patterns are lethal or cause disease, but the cues that normally designate CpG dinucleotides for methylation are poorly understood. Herein a new method of methylation profiling is disclosed that has single-CpG resolution and can address the methylation status of repeated sequences. We have used this method to determine the methylation status of >275 million CpG sites in human and mouse DNA from breast and brain tissues. Methylation density at most sequences was found to increase linearly with CpG density and to fall sharply at very high CpG densities, but transposons remained densely methylated even at very high CpG densities. The presence of histone H2A.Z and histone H3 di- or trimethylated at lysine 4 correlated strongly with unmethylated DNA and occurred primarily at promoter regions. Methylation is the default state of most CpG dinucleotides in the mammalian genome, and that a combination of local dinucleotide frequencies, the interaction of repeated sequences, and the presence or absence of histone variants or modifications shields a population of CpG sites (most of which are in and around promoters) from DNA methyltransferases that lack intrinsic sequence specificity.

REFERENCES

Alvarez R, Vasseur J-J, Beltran T, Imbach J-L (1999) Photocleavable Protecting Groups as Nucleobase Protections Allowed the Solid-Phase synthesis of Base-Sensitive SATEProoligonucleotides *J. Org. Chem* 64, 6319-6328.

Biniszkiewicz D, Gribnau J, Ramsahoye B, Gaudet F, Eggan K, Humpherys D, Mastrangelo M, Jun, Z, Walter J, Jaenisch R (2002) Dnmt1 Overexpression Causes Genomic Hypermethylation, Loss of Imprinting, and Embryonic Lethality *Mol Cell Biol.* 22, 2124-2135.

Church G M, Gilbert W. (1984) Genomic sequencing. Proc Natl Aced Sci USA. 81, 1991-1995.

Clark S J, Harrison J, Paul C L, Frommer M. (1994) High sensitivity mapping of methylated cytosines. Nucleic Acids Res. 22, 2990-2999.

Crookes M J and D L H Williams (1988) Nitrosation by alkyl nitrites. Part 2. Kinetics of reactions in aqueous acid solution with isopropyl and t-butyl nitrites *J. Chem. Soc., Perkin Trans.* 2 1339.

Dalhoff C, G Lukinavicius, S Klimasauskas and E Weinhold (2006a) Direct transfer of extended groups from synthetic cofactors by DNA methyltransferases *Nat Chem Biol* 2:31-2.

Dalhoff C, G Lukinavicius, S Klimasauskas and E Weinhold (2006b) Synthesis of S-adenosyl-Lmethionine analogs and their use for sequence-specific transalkylation of DNA by methyltransferases *Nat Protoc* 1, 1879-86.

De Napoli L, A Messere, D Montesarchio, G Picciall and M Varra (1997) 1-Substituted 2-deoxyinosine analogues *J. Chem. Soc., Perkin Trans.* 1, 2079-82.

Eads C A, Laird P W. (2002) Combined bisulfite restriction analysis (COBRA). Methods Mol Biol 200, 71-85.

Gitan R, Shi H, Chen C, Yan P, Huang T (2002) Methylation-Specific Oligonucleotide Microarray: A New Potential for High-Throughput Methylation Analysis *Genome Res.* 12, 158-164.

Goll, M. G., and Rector, T. H. (2004) Eukaryotic cytosine methyltransferases. Ann. Rev. Biochem. 74, 481-514.

Henry A A, C Yu and F E Romesberg (2003) Determinants of unnatural nucleobase stability and polymerase recognition *J Am Chem Soc* 125, 9638-46.

Henry A A and F E Romesberg (2003) Beyond A, C, G and T: augmenting nature's alphabet *Curr Opin Chem Biol* 7, 727-33.

Hikishima S, N Minakawa, K Kuramoto, Y Fujisawa, M Ogawa and A Matsuda (2005) Synthesis of 1,8-naphthyridine C-nucleosides and their base-pairing properties in oligodeoxynucleotides: thermally stable naphthyridine:imidazopyridopyrimidine base-pairing motifs *Angew Chem Int Ed Engl* 44:596-8.

Hikishima S, M Isobe, S Koyanagi, S Soeda, H Shimeno, S Shibuya and T Yokomatsu (2006) Synthesis and biological evaluation of 9-(5',5'-difluoro-5'-phosphonopentyl) guanine derivatives for PNP-inhibitors *Bioorg Med Chem* 14, 1660-70.

Holliday R, Pugh J E. (1975) DNA modification mechanisms and gene activity during development. Science 187, 226-232.

Ju J. D H Kim, L Bi, Q Meng, X Bai, Z Li, X Li, N B Mamma, S Shi, J Wu, J R Edwards, A Romu and N J Turro (2006) Four-color DNA sequencing by synthesis using cleavable fluorescent nucleotide reversible terminators *Proc Natl Acad Sci USA* 103, 19635-19640.

Liu H, J Gao, S R Lynch, Y D Saito, L Maynard and E T Kool (2003) A Four-Base Paired Genetic Helix with Expanded Size *Science* 302, 868-71.

Lorincz M, Schübeler D, Hutchinson S, Dickerson D, and Groudine M (2002) DNA Methylation Density Influences the Stability of an Epigenetic Imprint and Dnmt3a/b-Independent De Novo Methylation. Mol Cell Biol. 22, 7572-7580.

Matray T J and E T Kool (1999) A specific partner for abasic damage in DNA *Nature* 399, 704-708.

Miller C A, Sweatt J D. Covalent modification of DNA regulates memory formation. Neuron 53, 857-569.

Minakawa N, N Kojima, S Hikishima, T Sasaki. A Kiyosue, N Atsumi, Y Ueno and A Matsuda (2003) New Base Pairing Motifs. The Synthesis and Thermal Stability of Oligodeoxynucleotides Containing Imidazopyridopyrimidine Nucleosides with the Ability to Form Four Hydrogen Bonds *J. Am. Chem. Soc.* 125, 9970-82.

Minakawa N, Sasabuchi Y, Kiyosue A, Kojima M and Matsuda A (1996) *Chem. Pharm. Bull.* 44, 288.

Ohno S, K Mizukoshi, O Komatsu, Y Kunoh, Y Nakamura, B Katch and M Nagasaka (1986) Synthesis and Hypoglycemic Activity of 7,8-Dihydro-6H-thiopyrano[3,2-d] pyrimidine Derivatives and Related Compounds *Chemical & pharmaceutical bulletin* 34, 4150-65.

Panning B, Jaenisch R. (1996) DNA hypomethylation can activate Xist expression and silence Xlinked genes. Genes Dev. 10, 1991-2002.

Riggs A D. (1975) X inactivation, differentiation, and DNA methylation. Cytogenet Cell Genet. 14, 9-25.

Rollins R. Haghighi F, Edwards J, Das R, Zhang M, Ju J, and Bestor T H (2006) Large-scale structure of genomic methylation patterns Genome Res. 16, 157-163.

Ross S A, Pitie M, Meunier B (2000) A straightforward preparation of primary alkyl triflates and their utility in the synthesis of derivatives of ethidium. J. Chem. Soc., Perkin Trans. 1:571-574.

Sismour A M, S Lutz, J H Park, M J Lutz, P L Boyer, S H Hughes and S A Benner (2004) PCR amplification of DNA containing non-standard base pairs by variants of reverse transcriptase from Human Immunodeficiency Virus-1 *Nucleic Acids Res* 32, 728-35.

Steigerwald S D, Pfeifer G P, Riggs A D. (1990) Ligation-mediated PCR improves the sensitivity of methylation analysis by restriction enzymes and detection of specific DNA strand breaks. Nucleic Acids Res. 18, 1435-1439.

Stein R, Razin A, and Cedar H (1982) In vitro methylation of the hamster adenine phosphoribosyltransferase gene inhibits its expression in mouse L cells. Proc Natl Acad Sci USA. 79, 3418-3422.

Trinh B N, Long T I, Laird P W. (2001) DNA methylation analysis by MethyLight technology. Methods 25, 456-462.

Yamada Y, Jackson-Grusby L, Linhart H, Meissner A, Eden A, Lin H, Jaenisch R (2005) Opposing effects of DNA hypomethylation on intestinal and liver carcinogenesis *Proc Natl Aced Sci USA.* 102, 13580-13585.

Waalwijk C, Flavell R A. (1978) DNA methylation at a CCGG sequence in the large intron of the rabbit beta-globin gene: tissue-specific variations. Nucleic Acids Res 5, 4631-4634.

Warnecke P M, Stirzaker C, Song J, Grunau C, Melki J R, Clark S J. (2002) Identification and resolution of artifacts in bisulfite sequencing. Methods, 27, 101-107.

Warnecke P M, Stirzaker C, Melki J R, Millar D S, Paul C L, Clark S J. (1997) Detection and measurement of PCR bias in quantitative methylation analysis of bisulphite-treated DNA. Nucleic Acids Res. 25, 4422-426.

Wigler M, Levy D, Perucho M. (1981) The somatic replication of DNA methylation. Cell 24, 33-40.

Xu G L, Bestor T H. Bourc'his D, Hsieh C L, Tommerup N, Bugge M, Holten M, Qu X, Russo J J, Viegas-Pequignot E. (1999) Chromosome instability and immunodeficiency syndrome caused by mutations in a DNA methyltransferase gene. Nature 402, 187-91.

Yoder, J. A., Walsh, C. P., and Sector, T. H. (1997) Cytosine methylation and the ecology of intragenomic parasites. Trends Genet. 13, 335-340.

Stein R, Razin A, Cedar H. (1982) In vitro methylation of the hamster adenine phosphoribosyltransferase gene inhibits its expression in mouse L cells. Proc Natl Acad Sci USA 79: 61-67.

Lorincz M C, Schübeler D, Hutchinson S R, Dickerson D R, Groudine M. (2002) DNA methylation density influences the stability of an epigenetic imprint and Dnmt3a/b-independent de novo methylation. Mol Cell Biol 22: 7572-7580

Wigler M, Levy, D, Perucho M. (1981). The somatic replication of DNA methylation. Cell 24: 33-38

Jones P A, Wolkowicz M J, Rideout W M 3rd, Gonzales F A, Marziasz C M, at al. (1990) De novo methylation of the MyoD1 CpG island during the establishment of immortal cell lines. Proc Natl Aced Sci USA. 87:6117-21.

Rollins R A, Haghighi F, Edwards J R, Das R, Zhang at al (2006) Large-Scale Structure of Genomic Methylation Patterns. Genome Research, 16: 157-163.

Xu G. L, Bestor, T H, Bourc'his D., Hsieh C-L, Tommerup, N, et al. (1999) Chromosome instability and immunodeficiency syndrome caused by mutations in a DNA methyltransferase gene. Nature 402: 187-191

Sutcliffe J S, Nelson D L, Zhang, F, Pieretti, M, Caskey C T et al. (1992) DNA methylation represses FMR-1 transcription in fragile X syndrome. Hum Mol Genet 1: 1397-400.

Michaud, E. J., van Vugt, M. J., Bultman, S. J., Sweet, R. O., Davisson, M. T. (1994) et al. Differential expression of a new dominant agouti allele (Aiapy) is correlated with methylation state and is influenced by parental lineage. Genes Dev. 8: 1463-1472.

Rakyan V K, Preis J, Morgan H D, Whitelaw, E. (2001) The marks, mechanisms and memory of epigenetic states in mammals. Biochem J 15, 1-10.

Irizarry R A, Ladd-Acosta C, Carvalho B, Wu H, Brandenburg S A, (2008) Comprehensive high-throughput arrays for relative methylation (CHARM) Genome Res. 18:780-790

Weber N. Hellmann I, Stadler M B, Ramos L., Pääbo S., (2008) Distribution, silencing potential and evolutionary impact of promoter DNA methylation in the human genome. Nat Genet. 39: 457-466.

Kass S U, Landsberger N, Wolffe A P (1997) DNA methylation directs a time-dependent repression of transcription initiation. Curr Biol 7: 157-162.

Majewski J, Ott J (2002) Distribution and characterization of regulatory elements in the human genome. Genome Res 12: 1827-1833.

Kondrashov A S (2003) Direct estimates of human per nucleotide mutation rates at 20 loci causing Mendelian diseases. Hum Mutat 21: 12-18.

Young J I, Hong E P, Castle J C, Crespo-Barreto J, Bowman A B at al. (2005) Regulation of RNA splicing by the methylation-dependent transcriptional repressor methyl-CpG binding protein 2. Proc Natl Acad Sci USA 102: 17551-17556 (2005).

Barski A, Cuddapah S, Cui K, Roh T Y, Schones D E, at al. (2007) High-resolution profiling of histone methylations in the human genome. Cell 129, 823-830.

Mikkelsen T. S. Ku M, Jaffe D B, Issac B, Lieberman E, et al. (2007) Genome-wide maps of chromatin state in pluripotent and lineage-committed cells. Nature 448: 553-558.

Boyle A P, Davis S, Shulha H P, Meltzer P, Margulies E H, et al. (2008) High-resolution mapping and characterization of open chromatin across the genome. Cell 132, 311-317.

Ooi S K. Qiu C, Bernstein E, Li K, Jia D, et al. (2007) DNMT3L connects unmethylated lysine 4 of histone 53 to de novo methylation of DNA. Nature 448, 714-718.

Zilberman D, Coleman-Derr D, Ballinger T, Henikoff S. (2008) Histone H2A.Z and DNA methylation are mutually antagonistic chromatin marks. Nature 456: 125-129 (2008).

Bell A C, Felsenfeld G. (2000) Methylation of a CTCF-dependent boundary controls imprinted expression of the Igf2 gene. Nature 405: 482-488.

Hark, A. T. Schoenherr C J, Katz D J, Ingram R S, Levorse J M et al. (2000) CTCF mediates methylation-sensitive enhancer-blocking activity at the 519/Igf2 locus. Nature 405: 486-489

Walsh C P, Bestor T H. (1999) Cytosine methylation and mammalian development. Genes Dev. 13: 26-34.

Heintzman N D, Hon G C, Hawkins R D, Kheradpour P, Stark A, et al. (2009) Histone modifications at human enhancers reflect global cell-type-specific gene expression. Nature 459:108-112

Mohn F, Weber M, Rebhan M, Roloff T C, Richter et al. (2008) Lineage-specific polycomb targets and de novo DNA methylation define restriction and potential of neuronal progenitors. Mol Cell 30:755-766.

Meissner, A. Mikkelsen T S, Gu H, Wernig M, Hanna J, et al. (2008) Genome-scale DNA methylation maps of pluripotent and differentiated cells. Nature 454: 766-770.

Eckhardt, F. Lewin J, Cortese R, Rakyan V K, Attwood J, et al. (2006) DNA methylation profiling of human chromosomes 6, 20 and 22. Nat Genet 38: 1378-1382.

Down T A Rakyan V K, Turner D J, Flicek P, Li H, at al. (2008) A Bayesian deconvolution strategy for immunoprecipitation-based DNA methylome analysis. Nat. Biolech 26: 779-785.

Carmell M A, Girard A, van de Kant H J, Bourc'his D, Bestor T M, et al. (2007) M1W12 Is essential for spermatogenesis and repression of transposons in the mouse male germline. Dev. Cell 12: 503-514.

Lin I G, Tomzynski T J, Ou Q, Hsieh, C L. (2000) Modulation of DNA binding protein affinity directly affects target site demethylation. Mol Cell Biol. 20: 2343-2349.

Matsuo K Silke J, Georgiev O, Marti P, Giovannini N, et al. (1998) An embryonic demethylation mechanism involving binding of transcription factors to replicating DNA. EMBO J. 17: 1446-1453

What is claimed is:

1. A method of determining whether a cytosine present at a predetermined position immediately adjacent to a guanine within a single strand of a double-stranded DNA of known sequence is non-methylated comprising:

a) obtaining such a double-stranded DNA of known sequence comprising a cytosine at such predetermined position immediately adjacent to a guanine in such single strand;
b) producing a derivative of such double-stranded DNA by contacting the double-stranded DNA with a CpG methyltransferase and an s-adenosylmethionine analog having the structure:

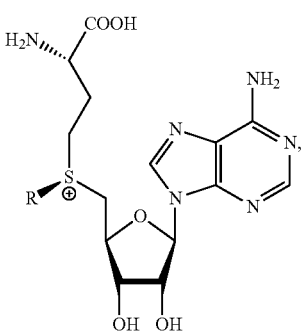

wherein R is a chemical group that is transferred from the s-adenosylmethionine analog by the CpG methyltransferase to a 5 carbon of a non-methylated cytosine within the double-stranded DNA so as to covalently bond the chemical group to the 5 carbon within the non-methylated cytosine of the double-stranded DNA, thereby making the derivative of the double stranded DNA;
c) separately obtaining a single strand of the derivative of the double-stranded DNA, wherein such single strand is the derivative of the single strand of the double-stranded DNA in which the cytosine is present at such predetermined position;
d) determining the sequence of the single strand of the derivative obtained in step c); and
e) comparing the sequence of the single strand of the derivative determined in step d) to the sequence of the strand of the double-stranded DNA in which the cytosine is present at such predetermined position, wherein the presence at such predetermined position in the single strand of the derivative of the double-stranded DNA of a thymidine analog instead of a cytosine indicates that the cytosine at such predetermined position in the single strand of the double-stranded DNA is non-methylated.

2. The method of claim 1, wherein the chemical group has the structure:

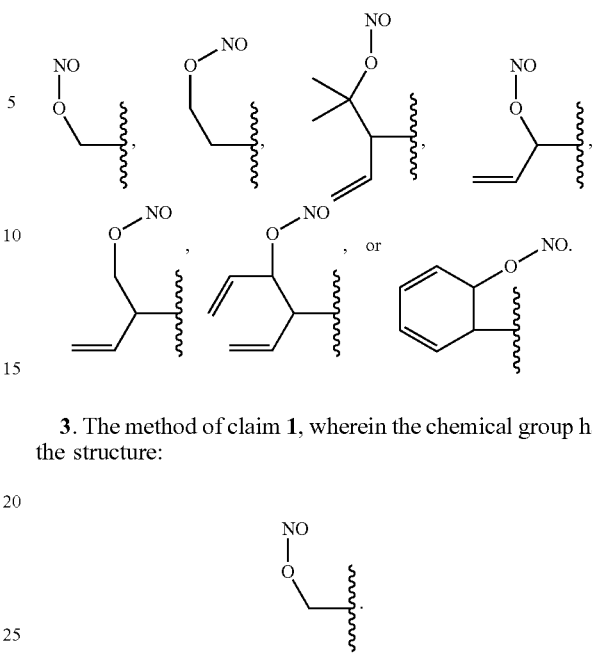

3. The method of claim 1, wherein the chemical group has the structure:

4. The method of claim 1, wherein the CpG methyltransferase is a SssI methyltransferase.

5. The method of claim 1, wherein the chemical group that is transferred from the s-adenosylmethionine analog by the CpG methyltransferase to the 5 carbon of the non-methylated cytosine of the double-stranded DNA undergoes oxidative deamination of a 4 position of the non-methylated cytosine when it is covalently bound to the 5 carbon of the non-methylated cytosine of the double-stranded DNA.

6. The method of claim 1, wherein in step d) the sequence of the single strand of the derivative is determined by sequencing by synthesis.

7. The method of claim 6, wherein the sequencing by synthesis comprises contacting the derivatized single strand with a DNA polymerase, a primer oligonucleotide dATP, dCTP, dGTP, dTTP, and a dideoxynucleotide triphosphate having a detectable label attached thereto.

8. The method of claim 7, wherein the detectable label is a radioactive or a fluorescent label.

9. The method of claim 7, wherein the detectable label is a mass tag.

10. The method of claim 1, further comprising attaching the single strand of the derivative to a solid support prior to step d).

* * * * *